(12) United States Patent
Kohno et al.

(10) Patent No.: US 6,610,502 B1
(45) Date of Patent: Aug. 26, 2003

(54) COMPOUND 2-AMINO-3-[2-(α-MANNOPYRANOSYL)INDOL-3-YL] PROPIONIC ACID, PROCESS FOR PREPARING THE SAME, AND METHOD FOR INSPECTING FUNCTION OF LIVING BODY WITH THE NOVEL COMPOUND

(75) Inventors: Hiroaki Kohno, Shizuoka (JP); Osamu Yonekawa, Shizuoka (JP); Yutaka Fujise, Shizuoka (JP); Kentaro Horiuchi, Shizuoka (JP); Kyoko Adachi, Shizuoka (JP); Hiroshi Sano, Kanagawa (JP)

(73) Assignees: Kyowa Medex Co., Ltd., Toyko (JP); Marine Biotechnology Institute Co., Ltd., Tokyo (JP)

( * ) Notice: Subject to any disclaimer, the term of this patent is extended or adjusted under 35 U.S.C. 154(b) by 0 days.

(21) Appl. No.: 09/486,115

(22) PCT Filed: Aug. 19, 1998

(86) PCT No.: PCT/JP98/03671

§ 371 (c)(1),
(2), (4) Date: Feb. 18, 2000

(87) PCT Pub. No.: WO99/09411

PCT Pub. Date: Feb. 25, 1999

(30) Foreign Application Priority Data

Aug. 20, 1997 (JP) ............................. 9-224065

(51) Int. Cl.$^7$ ................. G01N 33/577; G01N 33/535; C07H 7/06; C12N 5/20; C07K 16/18
(52) U.S. Cl. .................. 435/7.95; 435/345; 530/388.9; 530/389.8; 536/17.3
(58) Field of Search ............ 530/388.9, 389.8, 435/7.95, 345; 536/17.3

(56) References Cited

FOREIGN PATENT DOCUMENTS

| | | |
|---|---|---|
| JP | 6-220056 | 8/1994 |
| JP | 8-283179 | 10/1996 |
| WO | 97/27481 | 7/1997 |

OTHER PUBLICATIONS

J. Hofsteenge et al, Techniques in Protein Chemistry, Issue 7, 163–172, 1992.*
J. Hofsteenge et al, Biochemistry, 33, 13524–13530, 1994.*
T. De Beer et al, Biochemistry, 34, 11785–11789, 1995.*
E. Sevier et al, Clin. Chem. 27/11, 1797–1806, 1981.*
Harlow (ed.), Antibodies, A Laboratory Manual, Cold Spring Harbor, 141–143, 1988.*
Takahira, et al., "Tryptophan Glycoconjugate as a Novel Marker of Renal Function", The American Journal of Medicine, vol. 110 (2001), pp. 192–197.
Gutsche, et al. "Tryptophan Glycoconjugates in Food and Human Urine", Biochemical Society (1999), vol. 343, pp. 11–19.
Krieg, et al., "C–Mannosylation of Human Rnase Is an . . .", The Journal of Biological Chemistry, vol. 272, No. 42 (1997), pp. 26687–26692 .
Horiuchi, et al., Hydrophilic Tetrahydro–β–Carboline in Human Urine, J. Biochem. 115, 1994, pp. 362–366.

* cited by examiner

*Primary Examiner*—Mary E. Ceperley
(74) *Attorney, Agent, or Firm*—Fitzpatrick, Cella, Harper & Scinto

(57) ABSTRACT

The present invention relates to a novel endogenous compound 2-amino-3-[2-(α-mannopyranosyl)indole-3-yl] propionic acid; to a method for testing a biological function by quantitating 2-amino-3-[2-(α-mannopyranosyl)indole-3-yl]propionic acid in a collected biological sample and determining the biological function based on the quantitated values; to an antibody specifically reactive with 2-amino-3-[2-(α-mannopyranosyl)indole-3-yl]propionic acid; to a hybridoma that produces the antibody; to a method for immunologically quantitating 2-amino-3-[2-(α-mannopyranosyl)indole-3-yl]propionic acid in a sample by using the antibody; and to a process for producing a 2-amino-3-[2-(α-mannopyranosyl)indole-3-yl]propionic acid derivative.

14 Claims, 3 Drawing Sheets

COMPOUND 2-AMINO-3-[2-(α-MANNOPYRANOSYL)INDOL-3-YL] PROPIONIC ACID, PROCESS FOR PREPARING THE SAME, AND METHOD FOR INSPECTING FUNCTION OF LIVING BODY WITH THE NOVEL COMPOUND

TECHNICAL FIELD

The present invention relates to a novel endogenous compound 2-amino-3-[2-(α-mannopyranosyl)indole-3-yl] propionic acid which is useful for testing a biological function, to an antibody specifically reactive with the novel endogenous compound 2-amino-3-[2-(α-mannopyranosyl) indole-3-yl]propionic acid, to a hybridoma that produces the antibody, to a method for testing a biological function comprising quantitating the novel compound 2-amino-3-[2-(α-mannopyranosyl)indole-3-yl]propionic acid in a biological sample and determining the biological function based on the quantitated value, to a method for immunologically quantitating 2-amino-3-[2-(α-mannopyranosyl)indole-3-yl] propionic acid by using the antibody, and to a process for synthesizing 2-amino-3-[2-(α-mannopyranosyl)indole-3-yl] propionic acid.

BACKGROUND ART

Test of biological functions is very important, for example, for diagnosing diseases or for confirming therapeutic effects. For such test of biological function, various endogenous compound have been used as markers heretofore. Diseases are diagnosed or therapeutic effects are confirmed, based on the presence or concentration of the marker contained in a collected biological sample.

There have been demands for further detailed diagnosis of biological functions such as renal function, central nervous function and developmental function of fetus, and development of novel markers suitable for such diagnosis and development of uses thereof have been strongly demanded.

For example, glomerular filtration rate (hereinafter, abbreviated as "GFR") is one of the best indexes for testing renal functions. Accurate GFR can be measured by inulin clearance method. However, this measurement method is quite hard for the subject to bear, requiring patience and restraint of the subject. An alternative method is a creatinine clearance method which tests GFR based on creatinine levels in blood and creatinine excretion levels in urine. Creatinine can be easily quantitated by chemical or enzymatic methods. However, it is difficult to obtain accurate GFR by the creatinine clearance method since creatinine is secreted from uriniferous tubule; since its in vivo synthesis level is dependent on physiological parameters such as age, sex, body weight, obesity and the like; and since creatinine levels in blood and urine are increased due to intestine absorption of creatinine after ingestion of cooked meat or the like containing creatinine. Therefore, a novel index as an alternative to inulin and creatinine is strongly demanded.

DISCLOSURE OF THE INVENTION

The objects of the present invention are to provide a method for testing biological functions such as renal function, central nervous function and developmental function of fetus by quantitating a level of a novel endogenous compound; to provide a method for immunologically quantitating the novel endogenous compound; and to provide an antibody used therefor. Furthermore, the objects of the invention are to provide a process for producing the antibody used in the method for immunologically quantitating the novel endogenous compound; to provide a novel compound that can be used as an immunogen or as a hapten in the antibody production process; and to provide a process for synthesizing the novel compound. Moreover, the object of the present invention is to provide a novel intermediate for synthesis of the novel compound. The further object of the invention is to provide a hybridoma that produces an antibody to the novel endogenous compound.

The present inventors have analyzed various substances contained in biological samples by high-performance liquid chromatography, and found the existence of a novel fluorescent substance that appears at a high in vivo level in patients suffering from biological dysfunctions, for example, patients with renal dysfunction, pregnant patients with uremic syndrome and patients with central nervous dysfunction, thereby accomplishing the present invention.

The present invention relates to a method for testing a biological function, comprising: quantitating 2-amino-3-[2-(α-mannopyranosyl)indole-3-yl]propionic acid in a collected biological sample; and determining the biological function based on the quantitated value.

Examples of the above-mentioned biological function include a renal function, a central nervous function, and a developmental function of fetus. The biological sample is, for example, urine, serum, cerebrospinal fluid or amniotic fluid.

The present invention also relates to a method for immunologically quantitating 2-amino-3-[2-(α-mannopyranosyl) indole-3-yl]propionic acid, comprising immunologically quantitating 2-amino-3-[2-(α-mannopyranosyl)indole-3-yl] propionic acid in a sample by using an antibody specifically reactive with 2-amino-3-[2-(α-mannopyranosyl)indole-3-yl]propionic acid.

The present invention further relates to an antibody specifically reactive with 2-amino-3-[2-(α-mannopyranosyl) indole-3-yl]propionic acid. The antibody is, for example, a monoclonal antibody. The monoclonal antibody is, for example, monoclonal antibody KTM-250.

The present invention also relates to a hybridoma which produces a monoclonal antibody specifically reactive with 2-amino-3-[2-(α-mannopyranosyl)indole-3-yl]propionic acid. Examples of the hybridoma include hybridome KTM-250 (FERM BP-6432).

The present invention also relates to a 2-amino-3-[2-(α-D-mannopyranosyl)indole-3-yl]propionic acid derivative represented by general formula (XV):

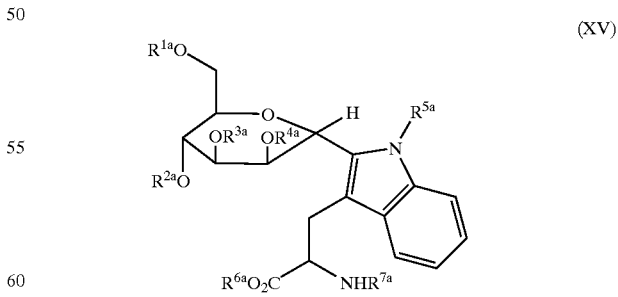

wherein $R^{1a}$ to $R^{4a}$, which may be the same or different, independently represent a hydrogen atom, a substituted or unsubstituted alkyl group, a substituted or unsubstituted alkenyl group, or a substituted or unsubstituted aryl group; $R^{5a}$ represents a hydrogen atom, a substituted or unsubstituted sulfamoyl group, a substituted or unsubstituted arylsulfonyl group, a substituted or unsubstituted alkoxycarbonyl group, or a substituted or unsubstituted alkoxymethyl group; $R^{6a}$ represents a hydrogen atom or a substituted or unsubstituted alkyl group; and $R^{7a}$ represents a hydrogen atom or a substituted or unsubstituted aralkyloxycarbonyl group, or 2-amino-3-[2-(α-L-mannopyranosyl)indole-3-yl] propionic acid derivative represented by general formula (XV'):

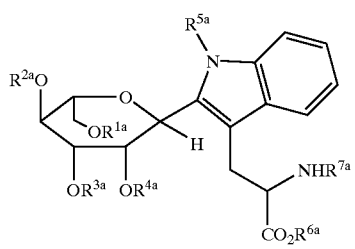

(XV')

wherein $R^{1a}$ to $R^{4a}$, which may be the same or different, independently represent a hydrogen atom, a substituted or unsubstituted alkyl group, a substituted or unsubstituted alkenyl group, or a substituted or unsubstituted aryl group; $R^{5a}$ represents a hydrogen atom, a substituted or unsubstituted sulfamoyl group, a substituted or unsubstituted arylsulfonyl group, a substituted or unsubstituted alkoxycarbonyl group, or a substituted or unsubstituted alkoxymethyl group; $R^{6a}$ represents a hydrogen atom or a substituted or unsubstituted alkyl group; and $R^{7a}$ represents a hydrogen atom or a substituted or unsubstituted aralkyloxycarbonyl group. Examples of the derivative include 2-amino-3-[2-(α-mannopyranosyl)indole-3-yl]propionic acid.

The present invention also relates to a process for producing an antibody to 2-amino-3-[2-(α-mannopyranosyl)indole-3-yl]propionic acid, wherein the process uses, as an immunogen or as a hapten, a 2-amino-3-[2-(α-D-mannopyranosyl)indole-3-yl]propionic acid derivative represented by general formula (XV):

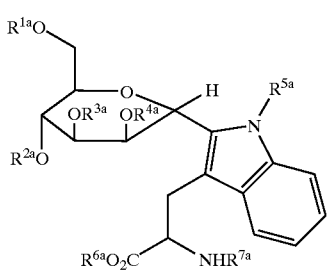

(XV)

wherein $R^{1a}$ to $R^{4a}$, which may be the same or different, independently represent a hydrogen atom, a substituted or unsubstituted alkyl group, a substituted or unsubstituted alkenyl group, or a substituted or unsubstituted aryl group; $R^{5a}$ represents a hydrogen atom, a substituted or unsubstituted sulfamoyl group, a substituted or unsubstituted arylsulfonyl group, a substituted or unsubstituted alkoxycarbonyl group, or a substituted or unsubstituted alkoxymethyl group; $R^{6a}$ represents a hydrogen atom or a substituted or unsubstituted alkyl group; and $R^{7a}$ represents a hydrogen atom or a substituted or unsubstituted aralkyloxycarbonyl group, or a 2-amino-3-[2-(α-L-mannopyranosyl)indole-3-yl] propionic acid derivative represented by general formula (XV'):

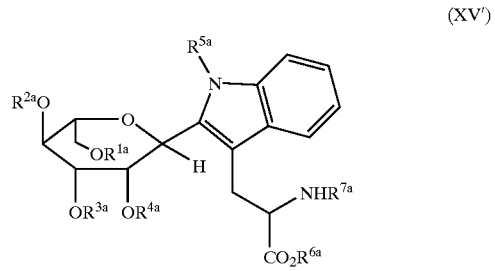

(XV')

wherein $R^{1a}$ to $R^{4a}$, which may be the same or different, independently represent a hydrogen atom, a substituted or unsubstituted alkyl group, a substituted or unsubstituted alkenyl group, or a substituted or unsubstituted aryl group; $R^{5a}$ represents a hydrogen atom, a substituted or unsubstituted sulfamoyl group, a substituted or unsubstituted arylsulfonyl group, a substituted or unsubstituted alkoxycarbonyl group, or a substituted or unsubstituted alkoxymethyl group; $R^{6a}$ represents a hydrogen atom or a substituted or unsubstituted alkyl group; and $R^{7a}$ represents a hydrogen atom or a substituted or unsubstituted aralkyloxycarbonyl groups. The above-described immunogen or hapten is, for example, 2-amino-3-[2-(α-mannopyranosyl)indole-3-yl] propionic acid.

The present invention also relates to a process for producing a 2-amino-3-[2-(α-D-mannopyranosyl)indole-3-yl] propionic acid derivative represented by general formula (XV):

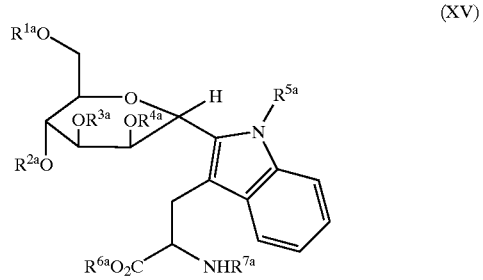

(XV)

wherein $R^{1a}$ to $R^{4a}$, which may be the same or different, independently represent a hydrogen atom, a substituted or unsubstituted alkyl group, a substituted or unsubstituted alkenyl group, or a substituted or unsubstituted aryl group; $R^{5a}$ represents a hydrogen atom, a substituted or unsubstituted sulfamoyl group, a substituted or unsubstituted arylsulfonyl group, a substituted or unsubstituted alkoxycarbonyl group, or a substituted or unsubstituted alkoxymethyl group; $R^{6a}$ represents a hydrogen atom or a substituted or unsubstituted alkyl group; and $R^{7a}$ represents a hydrogen atom or a substituted or unsubstituted aralkyloxycarbonyl group, or a 2-amino-3-[2-(α-L-mannopyranosyl)indole-3-yl]propionic acid derivative represented by the following formula (XV'):

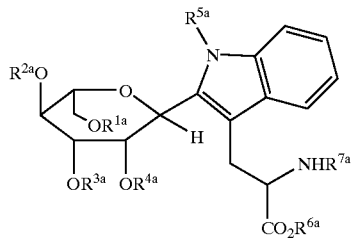

(XV')

wherein $R^{1a}$ to $R^{4a}$, which may be the same or different, independently represent a hydrogen atom, a substituted or unsubstituted alkyl group, a substituted or unsubstituted alkenyl group, or a substituted or unsubstituted aryl group; $R^{5a}$ represents a hydrogen atom, a substituted or unsubstituted sulfamoyl group, a substituted or unsubstituted arylsulfonyl group, a substituted or unsubstituted alkoxycarbonyl group, or a substituted or unsubstituted alkoxymethyl group; $R^{6a}$ represents a hydrogen atom or a substituted or unsubstituted alkyl group; and $R^{7a}$ represents a hydrogen atom or a substituted or unsubstituted aralkyloxycarbonyl group, the process comprising synthesizing a compound represented by general formula (IV)

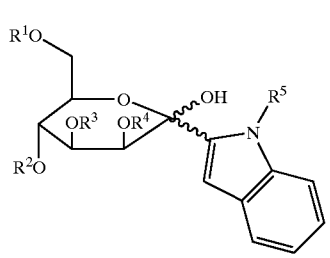

(IV)

wherein $R^1$ to $R^4$, which may be the same or different, independently represent a substituted or unsubstituted alkyl group, a substituted or unsubstituted alkenyl group, or a substituted or unsubstituted aryl group, or a compound represented by general formula (IV'):

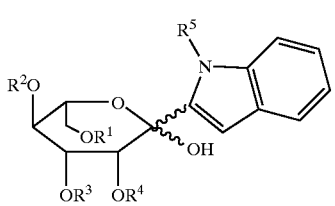

(IV')

wherein $R^1$ to $R^4$, which may be the same or different, independently represent a substituted or unsubstituted alkyl group, a substituted or unsubstituted alkenyl group, or a substituted or unsubstituted aryl group, by reacting a D-mannose derivative represented by general formula (I)

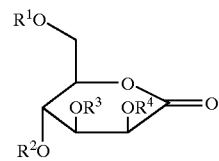

(I)

wherein $R^1$ to $R^4$, which may be the same or different, independently represent a substituted or unsubstituted alkyl group, a substituted or unsubstituted alkenyl group, or a substituted or unsubstituted aryl group, or a L-mannose derivative represented by general formula (I')

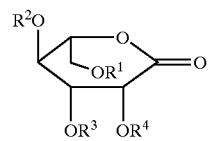

(I')

wherein $R^1$ to $R^4$, which may be the same or different, independently represent a substituted or unsubstituted alkyl group, a substituted or unsubstituted alkenyl group, or a substituted or unsubstituted aryl group, with an organometallic reagent represented by general formula (III)

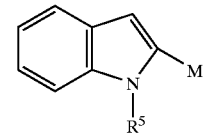

(III)

wherein $R^5$ represents a substituted or unsubstituted sulfamoyl group, a substituted or unsubstituted arylsulfonyl group, a substituted or unsubstituted alkoxycarbonyl group, or a substituted or unsubstituted alkoxymethyl group; and M represents a metal atom, a metal halide, an organometal or a metal salt. An example of the above-described product is 2-amino-3-[2-(α-mannopyranosyl)indole-3-yl]propionic acid.

Hereinafter, the compound represented by general formula (I) will be referred to as "compound (I)". Other compounds represented by different formulae will also be expressed likewise.

Physicochemical properties of the novel endogenous compound obtained according to the present invention are as follows:

(1) Color of the substance: colorless
(2) Mass spectrometry
m/z 365 [M−H]⁻, m/z 367 [M+H]⁺
Molecular weight: 366
(3) High resolution mass spectrometry
found: 367.1528 [M+H]⁺, calculated for $C_{17}H_{23}N_2O_7$: 367.1505
(4) Nuclear magnetic resonance spectrum
¹H-NMR (500 MHz, D₂O) δ: 3.35(1H, dd, J=8.8, 15.4 Hz; H-β), 3.55(1H, dd, J=5.1, 15.4 Hz; H-β), 3.74 (1H, dd, J=3.4, 12.7 Hz; H-6'), 3.90 (1H, ddd, J=3.4, 3.4, 9.0 Hz;

H-5'), 3.95 (1H, dd, J=3.4, 5.1 Hz; H-4'), 4.02 (1H, dd, J=5.1, 8.8 Hz; H-α), 4.12 (1H, dd, J=3.2, 5.1 Hz; H-3'), 4.25 (1H, dd, J=9.0, 12.7 Hz; H-6'), 4.43 (1H, dd, J=3.2, 8.3 Hz; H-2'), 5.18 (1H, d, J=8.3 Hz; H-1'), 7.22 (1H, dd, J=8.0, 8.0 Hz; H-5), 7.31 (1H, dd, J=8.0, 8.0 Hz; H-6), 7.53 (1H, d, J=8.0 Hz; H-7), 7.74 (1H, d, J=8.0 Hz; H-4).

$^{13}$C-NMR (125 MHz, D$_2$O) δ: 28.4 (C-β), 57.7 (C-α), 61.5 (C-6'), 68.6 (C-1'), 70.1 (C-2'), 71.3 (C-4'), 72.9 (C-3'), 81.4 (C-5'), 110.8 (C-3), 114.3 (C-7), 121.2 (C-4), 122.6 (C-5), 125.3 (C-6), 129.5 (C-3a), 135.8 (C-7a), 138.4 (C-2). 177.1 (COOH).

(5) Main absorption bands at infrared absorption spectrum (KBr method) cm$^{-1}$: 3400–3200, 2932, 1630, 1497, 1460, 1406, 1348, 1243, 1077, 1013, 748.

According to these data, the chemical structure of the novel endogenous compound of the invention was determined to be 2-amino-3-[2-(α-mannopyranosyl)indole-3-yl]propionic acid.

Hereinafter a process for producing 2-amino-3-[2-(α-mannopyranosyl)indole-3-yl]propionic acid will be described.

The novel endogenous compound of the invention can be obtained from a body fluid such as urine, serum or cerebrospinal fluid from animals through its isolation and purification. The compound may be isolated and purified by routine methods utilizing physicochemical differences such as differences in molecular weights, charges, polarities, hydrophobicities, adsorption coefficients, distribution coefficients, solubilities in various solutions and specific affinities.

Purification is conducted according to known methods using various chromatographies (e.g., column chromatography or thin-layer chromatography). Examples of the chromatography include ion-exchange chromatography, gel-filtration chromatography, adsorption column chromatography, partition column chromatography, hydrophobic chromatography and isoelectric chromatography, which may be used alone or in combination. High-performance liquid column chromatography may also be employed. Procedures involved in the chromatography such as desalting, concentration and extraction may be performed according to conventional methods.

Insoluble substances such as precipitates or high-molecular-weight compounds such as proteins contained in the collected biological sample are preferably removed prior to the chromatography process. The insoluble substances such as precipitates can be removed, for example, by centrifugation or filtration. The high-molecular-weight compounds like proteins can be removed, for example, by denaturation with organic solvents or the like, or by heat treatment.

The novel endogenous compound of the invention can be detected upon the above-described isolation and purification process, for example, by high-performance liquid column chromatography under the following conditions:

Column: Finepak SIL C18-T5 (4 mm×25 cm, JASCO Corporation)

Development solvent: a mixed solvent of acetonitrile and a buffer (70 mM citric acid: 60 mM disodium phosphate=1:1, v/v, pH 3.5)
  0 to 1.5 min.; acetonitrile:buffer=96:4 (v/v)
  1.5 to 7.0 min.; acetonitrile:buffer=92:8 (v/v)
  7.0 to 25.0 min.; acetonitrile:buffer=88:12 (v/v)

Temperature: room temperature

Flow rate: 1.5 ml/min.

Detection: Fluorescence, excited at 302 nm, determined at 350 nm

Retention time: about 6.8 minutes

Compounds (XIII) and (XIIII) of the present invention may be obtained by synthesis described below. According to the present invention, compounds (XIXX) and (XIII') are obtained when the D-mannose derivative represented by formula (I) and L-mannose derivative represented by formula (I') are used as starting materials, respectively. Compound (XIII) contains (2R)-2-amino-3-[2-(α-D-mannopyranosyl)indole-3-yl]propionic acid and (2S)-2-amino-3-[2-(α-D-mannopyranosyl)indole-3-yl]propionic acid) while compound (XIII') contains (2R)-2-amino-3-[2-(α-L-mannopyranosyl)indole-3-yl]propionic acid and (2S)-2-amino-3-[2-(α-L-mannopyranosyl)indole-3-yl]propionic acid.

A synthesis pathway for producing compound (XIII) from compound (I) via compound (IV) and a synthesis pathway for producing compound (XIII') from compound (I') via compound (IV') are shown below, respectively. Since compound (I') is an enantiomer of compound (I), compound (XIII') may be obtained from compound (I') via compound (IV') through the similar synthesis pathway. Compounds represented by formulae (XV) and (XV') are obtained by synthesis according to the reaction pathway of this synthesis.

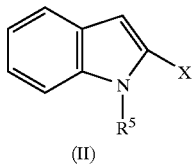

(II)

Step 1

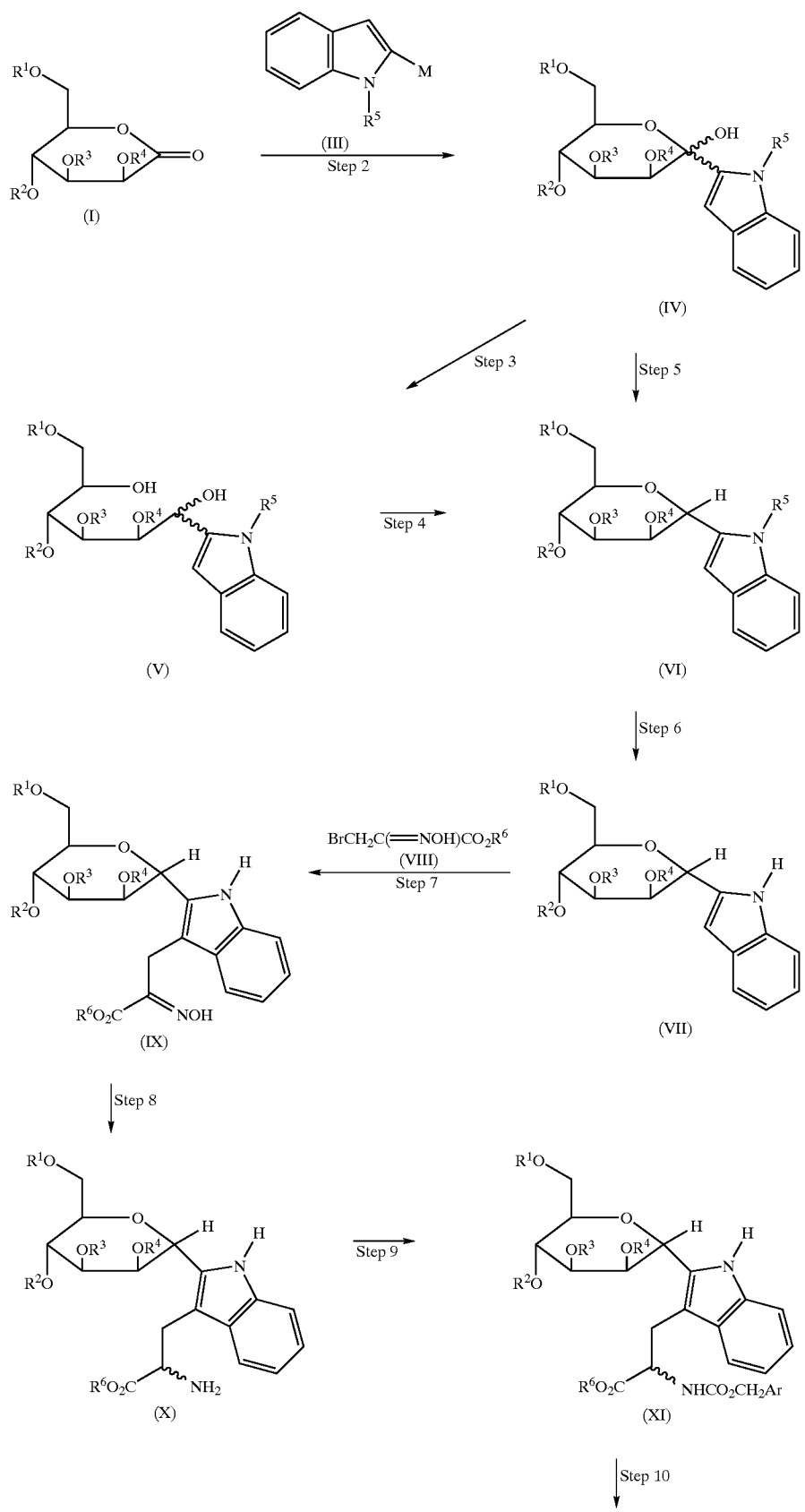

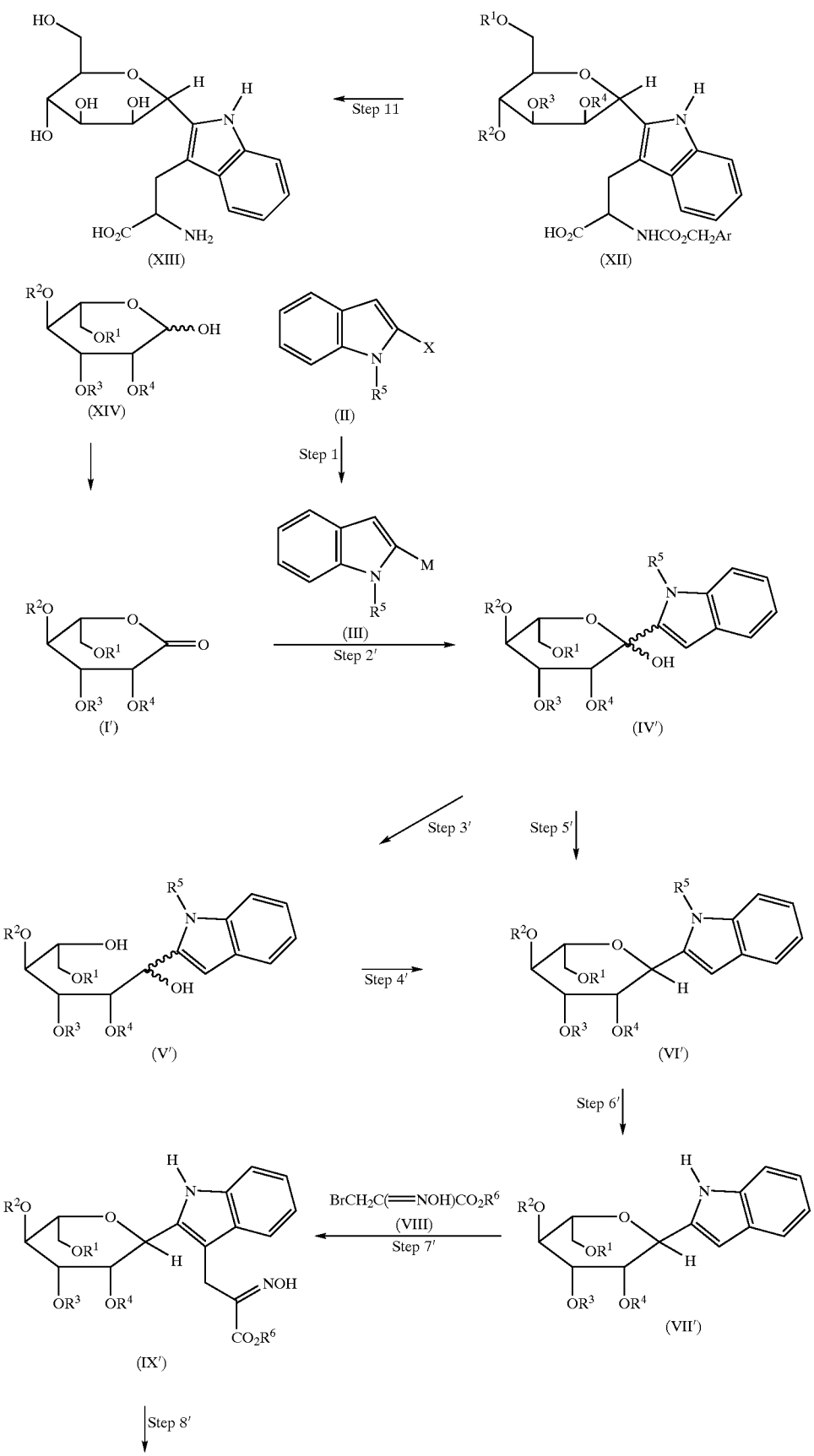

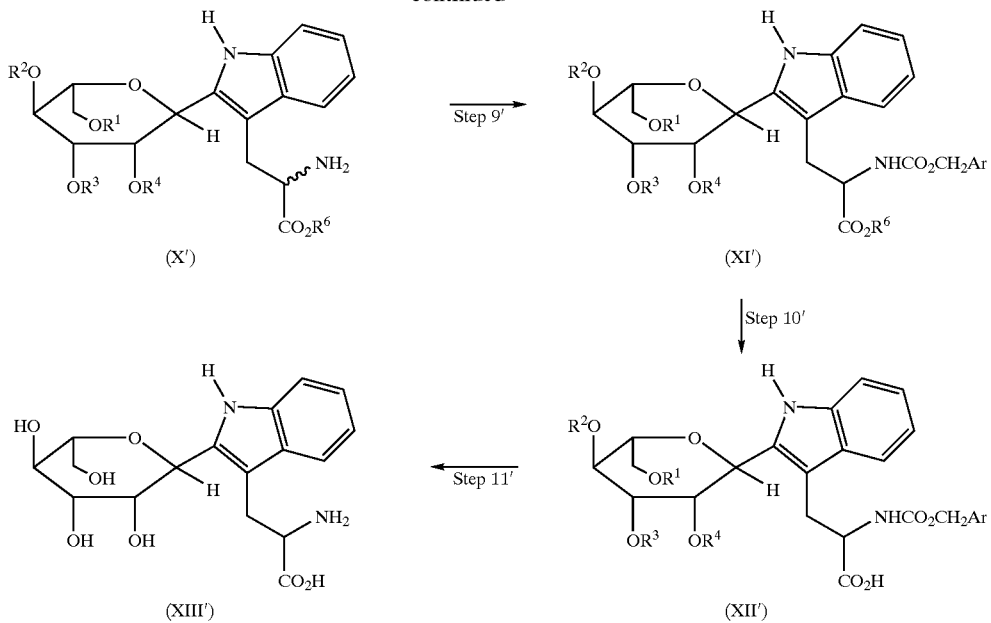

(X')  (XI')  (XII')  (XIII')

wherein $R^1$ to $R^4$, which may be the same or different, independently represent a substituted or unsubstituted alkyl group, a substituted or unsubstituted alkenyl group or a substituted or unsubstituted aryl group; $R^5$ represents a substituted or unsubstituted sulfamoyl group, a substituted or unsubstituted arylsulfonyl group, a substituted or unsubstituted alkoxycarbonyl group or a substituted or unsubstituted alkoxymethyl group; X represents a hydrogen atom or a halogen atom; M represents a metal atom, a metal halide, an organometal or a metal salt; $R^6$ represents a substituted or unsubstituted alkyl group; and Ar represents a substituted or unsubstituted aryl group.

In defining each of the above-mentioned groups, examples of alkyl moieties of the alkyl, alkoxycarbonyl and alkoxymethyl groups include linear or branched $C_{1-6}$ alkyl groups such as methyl, ethyl, propyl, isopropyl, butyl, isobutyl, sec-butyl, tert-butyl, pentyl, 2-pentyl, 3-pentyl, isoamyl and hexyl groups.

Examples of the alkenyl group include linear or branched $C_{2-6}$ alkenyl groups such as vinyl, 1-propenyl, 2-propenyl (allyl), butenyl, pentenyl and hexenyl groups.

Aryl moiety of the aryl or aralkyloxycarbonyl group represents a phenyl group, a naphthyl group, or the like. Alkylene moiety of the aralkyloxycarbonyl group represents a moiety formed by removing one hydrogen atom from the above-described alkyl group.

Substituents of the substituted alkyl or alkenyl group, which may be the same or different, include an aryl group, an alkoxy group, an amide group, an amino group, a halogen atom, a carboxyl group, a nitro group, a hydroxy group, a sulfo group and the like. In this case, the number of the substituents may be 1 to 3.

Substituents of the substituted aryl group, substituents on the aryl of the substituted arylsulfonyl group or the substituents on the aryl of the substituted aralkyloxycarbonyl group, which may be the same or different, include an alkyl group, an alkoxy group, an amide group, an amino group, a halogen atom, a carboxyl group, a nitro group, a hydroxy group, a sulfo group and the like. In this case, the number of substituents may be 1 to 3.

Substituents on the nitrogen atom of the substituted sulfamoyl group, which may be the same or different, include a substituted or unsubstituted aryl group, a substituted or unsubstituted alkyl group and the like. In this case, the number of substituents may be 1 to 2. The substituents of the substituted aryl and alkyl groups are as described above.

Examples of the substituted alkoxycarbonyl group include methoxycarbonyl, tert-butoxycarbonyl and 2,2,2-trichloroethoxycarbonyl groups.

Examples of the substituted alkoxymethyl group include methoxymethyl and 2-trimethylsilylethoxymethyl groups.

The halogen atom refers to a fluorine, chlorine, bromine or iodine atom.

The alkyl moiety of the alkoxy group has the same meanings as the above-described alkyl group.

Preferably, $R^1$ to $R^4$ of compounds (I) and (I') independently represent a benzyl group. D-mannose derivative (I) may be synthesized, for example, by the method described in *J. Am. Chem. Soc.*, 104, 4976 (1982). L-mannose derivative (I') may be synthesized, for example, from compound (XIV) as described in *J. Med. Chem.*, 29, 1945 (1986) [wherein $R^1$ to $R^4$ independently represent a benzyl group], for example, by the method described in *J. Am. Chem. Soc.*, 104, 4976 (1982).

Step 1

Organometallic reagent (III) can be prepared from compound (II) in the following manner:

(i) Reacting compound (II), wherein X is a hydrogen atom, with an organolithium reagent (proton-metal exchange reaction); (ii) reacting compound (II), wherein X is a halogen atom, with a metal itself or an organometallic reagent (halogen-metal exchange reaction); and (iii) reacting the organometallic reagent prepared in (i) or (ii) with an inorganic metal salt or organometallic compound (metal-metal exchange reaction).

M of organometallic reagent (III) may be a lithium atom, a magnesium salt, a cerium salt, a zinc salt, a copper salt, a mercury salt or the like, preferably a lithium atom.

The organometallic reagent (III), wherein M is a lithium atom, may be prepared from compound (II) and an organolithium reagent. When compound (II), wherein X is a hydrogen atom, is used, the organolithium reagent may be n-butyllithium, lithium diisopropylamide, sec-butyllithium, sec-butyllithium-tetramethylethylenediamine or tert-butyllithium, preferably lithium diisopropylamide. When compound (II), wherein X is a halogen atom, is used, n-butyllithium, sec-butyllithium, sec-butyllithium-tetramethyl ethylenediamine or tert-butyllithium may be used as the organolithium reagent. The organolithium reagent may be used in an amount of 0.7 to 1.0 equivalent, preferably 0.8 to 0.9 equivalent relative to the amount of compound (II).

The reaction temperature is $-100°$ C. to $-60°$ C., preferably $-80°$ C. to $-70°$ C. The reaction time varies depending on the organolithium reagents used, and generally is 5 to 30 min.

Step 2 or 2'

Compound (IV) or (IV') may be obtained by respectively reacting compound (I) or (I') with organometallic reagent (III). Organometallic reagent (III) is used in an amount of 1.1 to 3.0 equivalents, preferably 1.2 to 1.4 equivalents relative to the amount of compound (I) or (I').

The reaction solvent may be an ether solvent such as diethylether or tetrahydrofuran, or a hydrocarbon solvent such as n-hexane or toluene, the solvents being used alone or in mixture.

The reaction temperature is $-100°$ C. to $-60°$ C., preferably $-80°$ C. to $-70°$ C. The reaction time is 10 min. to 2 hours, generally about 30 min.

The reaction may be followed by a series of steps generally employed in organic synthesis reactions, i.e., termination of the reaction, phase separation, extraction and concentration: for example, termination of the reaction by addition of an aqueous saturated ammonium chloride solution or the like, extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 3 or 3'

Compound (V) or (V') can be obtained by respectively reacting compound (IV) or (IV') with a reducing agent. The reducing agent is used in an amount of 3.0 to 10.0 equivalents, preferably 3.0 to 4.0 equivalents relative to the amount of compound (IV) or (IV').

The reducing agent may be a metal-hydrogen complex compound such as lithium aluminum hydride or sodium borohydride, preferably lithium aluminum hydride.

The reaction solvent, although it varies depending on the bases used, may be an ether solvent such as diethyl ether or tetrahydrofuran, or optionally a protonic solvent such as methanol, the solvents being used alone or in mixture.

The reaction temperature, although it may vary depending on the bases used, may be $-40°$ C. to room temperature, generally $0°$ C. to room temperature. The reaction time, although it may vary depending on the reaction temperatures and the bases used, is generally 30 min. to 2 hours.

The reaction may be followed by a series of steps employed in organic synthesis reactions, i.e., termination of the reaction, phase separation, extraction and concentration: for example, termination of the reaction by addition of an aqueous saturated Rochelle salt solution or the like, extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 4 or 4'

Compound (VI) or (VI') can be obtained by respectively reacting compound (V) or (V') with an acid. The acid is used in an amount of 0.1 to 1.0 equivalent, preferably 0.5 to 0.6 equivalent relative to the amount of compound (V) or (V').

The acid may be an organic acid such as par-toluene sulfonate or camphor sulfonate, or an inorganic acid such as sulfuric acid or hydrochloric acid, preferably para-toluene sulfonate.

The reaction solvent may be an aromatic hydrocarbon solvent such as toluene or benzene, or a halogenated hydrocarbon solvent such as dichloromethane or chloroform, preferably toluene.

The reaction temperature, although it may vary depending on the acids used, is generally a temperature around the boiling point of the solvent used. The reaction time, although it may vary depending on the acids used, is generally 1 to 2 hours.

The reaction may be followed by a series of steps employed in organic synthesis reactions, i.e., termination of the reaction, phase separation, extraction and concentration: for example, termination of the reaction by addition of an aqueous saturated sodium hydrogencarbonate solution or the like, extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 5 or 5'

Alternatively, compound (VI) or (VI') can also be obtained by respectively reacting compound (IV) or (IV') with a reducing agent in the presence of an acid. The acid is used in an amount of 1 to 50 equivalents, preferably 10 to 15 equivalents relative to the amount of compound (IV) or (IV'). The reducing agent is used in an amount of 1.0 to 5.0 equivalents, preferably 1.5 to 2.0 equivalents relative to the amount of the acid.

The acid may be Lewis acid such as boron trifluoride diethyl etherate or zinc chloride, or a protonic acid such as sulfuric acid, acetic acid or trifluoroacetic acid, preferably boron trifluoride diethyl etherate.

The reducing agent may be triethylsilane or the like.

The reaction solvent may be a non-protonic polar solvent such as acetonitrile, an aromatic hydrocarbon solvent such as toluene or benzene, or a halogenated hydrocarbon solvent such as dichloromethane or chloroform.

The reaction temperature, although it may vary depending on the solvents used, is $-100°$ C. to a temperature around the boiling point of the solvent used, generally $-78°$ C. or $-40°$ C. to room temperature. The reaction time is generally 10 to 20 hours.

The reaction may be followed by a series of steps generally employed in organic synthesis reactions, i.e., termination of the reaction, phase separation, extraction and concentration: for example, termination of the reaction by addition of an aqueous saturated sodium hydrogencarbonate solution or the like, extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 6 or 6'

Compound (VII) or (VII') can be obtained by respectively reacting compound (VI) or (VI') with an excessive amount of a base. The base is preferably used in an amount of 50 to 150 equivalents relative to the amount of compound (VI) or (VI').

The base may be alkali metal hydroxide such as lithium hydroxide, sodium hydroxide and potassium hydroxide, alkali metal alkoxide such as sodium methoxide, sodium ethoxide and potassium tert-butoxide, alkali metal carbonate such as sodium carbonate and potassium carbonate, or the like.

The reaction solvent may be a mixed solvent of water and an alcohol such as methanol, ethanol or isopropanol, or a mixed solvent of water and an ether solvent such as diethylether, tetrahydrofuran or 1,2-dimethoxyethane.

The reaction temperature is not specifically limited, but preferably a temperature around the boiling point of the solvent used. The reaction time, although it varies depending on the bases and solvents used, is generally 1 to 20 hours.

The reaction may be followed by a series of steps generally employed in organic synthesis reactions, i.e., termination of the reaction, phase separation, extraction and concentration: for example, addition of an aqueous saturated ammonium chloride solution or the like, followed by extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Alternatively, compound (VII) or (VII') may also be obtained by respectively reacting compound (VI) or (VI') with a reducing agent.

The reducing agent may be a metal-hydrogen complex compound such as lithium aluminum hydride or sodium borohydride, or a metal such as magnesium or zinc, the reducing agent being used optionally in the presence of an inorganic salt such as ammonium chloride or an acid such as hydrochloric acid.

The reaction solvent, although it varies depending on the reducing agents used, may be an ether solvent such as diethylether and tetrahydrofuran, or optionally a protonic solvent such as methanol.

The reaction temperature, although it may vary depending on the reducing agents used, is generally room temperature to a temperature around the boiling point of the solvent used. The reaction time, although it differs depending on the reducing agents used, is generally 2 to 24 hours.

The reaction may be followed by a series of steps generally employed in organic synthesis reactions, i.e., termination of the reaction, phase separation, extraction and concentration: for example, addition of an aqueous saturated ammonium chloride solution or the like, followed by extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 7 or 7'

Compound (IX) or (IX') can be obtained by respectively reacting compound (VII) or (VII') with compound (VIII) in the presence of a base. Compound (VIII) may be synthesized according to the method described in *J. Chem. Soc., Chem. Commun.*, 1089 (1979). Compound (VIII) is used in an amount of 1.0 to 10 equivalents, preferably 2.0 to 2.5 equivalents relative to the amount of compound (VII) or (VII'), and the base is used in an amount of 1.0 to 10 equivalents, preferably 1.5 to 2.0 equivalents relative to the amount of compound (VIII).

Examples of the base include alkali metal carbonate such as sodium carbonate and potassium carbonate.

The reaction solvent may be a halogenated hydrocarbon solvent such as dichloromethane, chloroform or 1,2-dichloroethane.

The reaction temperature is, but not limited to, 0° C. to a temperature around the boiling point of the solvent, preferably a temperature around room temperature. The reaction time, although it varies depending on the reaction solvents and bases used, is generally 1 to 2.5 hours.

The reaction may be followed by a series of steps generally employed in organic synthesis reactions, i.e., termination of the reaction, phase separation, extraction and concentration: for example, addition of an aqueous saturated ammonium chloride solution or the like, followed by extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 8 or 8'

Compound (X) or (X') can be obtained by respectively reacting compound (IX) or (IX') with a reducing agent.

The reducing agent is preferably an amalgam such as aluminum-amalgam or the like. The reaction may be a catalytic reduction using a heterogeneous catalyst such as palladium-carbon, palladium hydroxide-carbon or platinum oxide under an atmosphere of hydrogen gas.

The reaction solvent may be a mixed solvent of water and an ether solvent such as diethyl ether, tetrahydrofuran or 1,2-dimethoxyethane.

The reaction temperature is, but not limited to, 0° C. to a temperature around the boiling point of the solvent used, preferably room temperature to 60° C. The reaction time, although it varies depending on the solvents used, is generally 0.5 to 1.0 hour.

The reaction may be followed by a series of steps generally employed in organic synthesis reactions, i.e., termination of the reaction, phase separation, extraction and concentration: for example, filtration of the reaction mixture with celite or the like, addition of an aqueous saturated sodium hydrogencarbonate solution or the like to the filtrate, extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 9 or 9'

Compound (XI) or (XI') can be obtained by respectively reacting compound (X) or (X') with arylmethyl chloroformate in the presence of a base. The arylmethyl chloroformate is used in an amount of 1.0 to 10 equivalents, preferably 2.0 to 2.5 equivalents relative to the amount of compound (X) or (X'). The base is used in an amount of 1.0 to 10 equivalents, preferably 2.0 to 3.0 equivalents relative to the amount of compound (X) or (X').

Examples of the base include organic bases such as triethylamine and pyridine, preferably triethylamine.

Examples of the solvent include halogenated hydrocarbon solvents such as dichloromethane, chloroform and 1,2dichloroethane, and aromatic hydrocarbon solvents such as benzene and toluene, preferably chloroform.

The reaction temperature, although it is not specifically limited, is preferably −100° C. to room temperature, more preferably −20° C. to room temperature. The reaction time is generally 10 min. to 1.0 hour.

The reaction may be followed by a series of steps generally employed in organic synthesis reactions, i.e., termination of the reaction, phase separation, extraction and concentration: for example, addition of an aqueous saturated sodium hydrogencarbonate solution or the like, extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 10 or 10'

Compound (XII) or (XII') can be obtained by hydrolyzing compound (XI) or (XI') with a base, respectively. The base is used in an amount of 1.0 to 10 equivalents, preferably 3.0 to 4.0 equivalents relative to the amount of compound (XI) or (XI').

Examples of the base include alkyl metal hydroxides such as lithium hydroxide, sodium hydroxide and potassium hydroxide.

The reaction solvent may be a mixed solvent of water and an ether solvent such as diethyl ether, tetrahydrofuran or 1,2-dimethoxyethane, or a mixed solvent of water and an alcoholic solvent such as methanol or ethanol.

The reaction temperature, although it is not specifically limited, is preferably a temperature around room temperature. The reaction time is generally 10 to 24 hours.

The reaction may be followed by a series of steps generally employed in organic synthesis reactions, i.e., termination of the reaction, phase separation, extraction and concentration: for example, addition of an aqueous citric acid solution or the like, extraction with an organic solvent such as ether, ethyl acetate or dichloromethane, drying over anhydrous sodium sulfate or anhydrous magnesium sulfate, and removal of the solvent with a vacuum rotatory evaporator. The compound may be separated/purified by column chromatography, preparative thin-layer chromatography or the like.

Step 11 or 11'

Compound (XIII) or (XIII') can be obtained by respectively subjecting compound (XII) or (XII') to a hydrogenation using a catalyst under an atmosphere of hydrogen gas.

The catalyst may be a heterogeneous catalyst such as palladium-carbon, palladium hydroxide-carbon or platinum oxide, preferably palladium hydroxide-carbon.

The reaction solvent may be a protonic solvent such as methanol, ethanol or isopropanol, or a non-protonic solvent such as ethyl acetate or N,N-dimethylformamide, the solvents being used alone or in combination. Preferably, the reaction solvent is ethanol.

The reaction temperature is not specifically limited, but it is preferably at room temperature to a temperature around the boiling point of the solvent used, more preferably room temperature to 60° C. The reaction time is generally 10 to 15 hours.

The reaction may be followed by operations generally employed in hydrogenation: for example, filtration of the reaction mixture with celite or the like, followed by removal of the solvent with a vacuum rotation evaporator. The synthesized compound may be separated/purified by high-performance liquid column chromatography or the like.

The intermediates obtained by the above steps may directly be used in the subsequent reactions without purification. In the synthesis of the invention, compound (XIII) or (XIII') may be obtained in the pure form by isolating/purifying the compound obtained in step 11 or 11', or preferably by separating/purifying compound (XII) or (XII') obtained in step 10 or 10' by column chromatography, preparative thin-layer chromatography or the like followed by subjecting to the reaction of step 11 or 11'.

Hereinafter, an antibody that is specifically reactive with 2-amino-3-[2-(α-mannopyranosyl)indole-3-yl]propionic acid of the invention will be described.

A process for producing the antibody of the invention is as follows. An antibody to 2-amino-3-[2-(α-mannopyranosyl)indole-3-yl]propionic acid may be produced by using compound (XV) or (XV') as an immunogen or a hapten. When compound (XV) or (XV') is used as a hapten, a complex obtained by binding compound (XV) or (XV') to a high-molecular-weight carrier can be used as an immunogen. Compound (XV) or (XV') may be used which is obtained by purifying the compound obtained according to the synthetic method described above. Specifically, 2-amino-3-[2-(α-mannnopyranosyl)indole-3-yl]propionic acid may be purified from a biological sample according to the method described above or may be synthesized according to the synthetic method described above.

The high-molecular-weight carrier may be any substance as long as it has a reactive group that can effect a condensation reaction with the carboxyl group, amino group, hydroxy group or the like of compound (XV) or (XV') and 2-amino-3-[2-(α-mannopyranosyl)indole-3-yl]propionic acid, and as long as it can confer immunogenicity to the compound or it enhances the originally-existing immunogenicity of the compound by linking with the novel tryptophan derivatives. Particular examples of the carrier are bovine serum albumin (hereinafter, abbreviated as "BSA"), protein such as globulin, keyhole limpet hemocyanine (hereinafter, abbreviated as "KLH") or thyroglobulin, polysaccharides such as dextran or sepharose, latex particules such as polystylene or acryls, polynucleic acids such as polyuridylic acid or polyalanylic acid, and synthetic polymer such as MAP. These high-molecular-weight substances may be linked with the tryptophan derivatives of the invention according to the methods described by Nobuo Sakado [Procedures for *Immunological Experiments* 151, Shunsuke Migita et al. (ed.), Nankodo (1995)] such as methods using amino group (e.g., carbodiimide method, glutaraldehyde method, and diisocyanate method), methods using carboxyl group (e.g., activated ester method, mixed anhydride method, and acyl azide method), methods using SH group (e.g., MBS and SPDP methods), and methods using hydroxy group (e.g., cyanogen bromide method and periodate oxidation method).

Examples of animals that may be immunized with the immunogen obtained above include mouse, rat, hamster, rabbit, guinea pig, goat, sheep and chicken. In preparation of polyclonal antibodies the preferred animals are rabbit, guinea pig, goat, sheep and chicken while mouse and rat in preparation of a monoclonal antibodies.

Immunization may be conducted according to the method described by Nishimichi and Toyoshima (*New Biochemical Experiments*, 1, 389 (1990), Tokyo Kagaku Dojin). For example, the immunogen is emulsified in Freund's complete or incomplete adjuvant, and administered intraperitoneally, subcutaneously or intramuscularly. For example, immunization may be completed by administering the immunogen twice or more, preferably 2 to 4 times, constantly at 7–30 day intervals, preferably 12–16 day intervals. In obtaining a polyclonal antibody, blood is taken from the completely immunized animal by periodic bleeding or by bleeding of the whole blood. Generally, blood is collected without prevention of coagulation, and is allowed to coagulate prior to recovery of serum fraction by centrifugation or the like.

The antibody contained in the blood may be used, if necessary, after purification. Purification may be conducted by various methods including salting-out fractionation using ammonium sulfate or the like, ion exchange chromatography, gel filtration column chromatography, affinity column chromatography using protein A or G, or affinity column chromatography using antigen-immobilized gel, the methods being used alone or in combination.

In obtaining a monoclonal antibody, the antibody-producing cells may be collected from sources such as spleen, lymph node or peripheral blood of immunized animals. Alternatively, the antibody-producing cells may also be obtained by the so-called in vitro immunization [Arai and Ohta, *Experimental Medicine*, 6:43 (1988)] which comprises removing an antibody-producing competent cell from the spleen, lymph node or peripheral blood of a non-immunized animal, then subjecting the competent cell to a direct immunization.

Myeloma cells fused with the antibody-producing cells are not specifically limited, but preferably are cell lines derived from the same animal as the animal from which the antibody-producing cells are derived. In order to efficiently select only the cells that succeeded in cell fusion, the myeloma cells preferably contain a specific drug marker. For example, a myeloma cell resistant to 8-azaguanine is favored for although it cannot grow in a medium containing hypoxanthine, aminopterin and thymidine (hereinafter, referred to as "HAT medium"), whereas it can grow in HAT medium when it is fused with a normal cell, drawing a distinction between fused and unfused myeloma cells. Specific examples of myeloma cells include P3×63–Ag.8.653, P3×63–Ag.8.U1 (hereinafter, simply referred to as "P3U1") and Sp/O-Ag14.

Cell fusion was first developed by Kohler and Milstein [*Nature*, 256, 495 (1975)], which then rapidly diffused, and various improved methods thereof are currently applicable. According to the common method, the antibody-producing cell and the myeloma cell are mixed in a proportion of 10-3:1 while using 30–50% polyethylene glycol (average molecular weight of 1,500–6,000) as a fusing agent. Their cells may also be fused by an electric pulse [Kawauchi et al., *Experimental Medicine*, 6, 50 (1988)].

At the end of cell fusion, the cells are suspended in the selective medium and only the fusion cells are grown in a culture container (e.g., a 96-well plate) advantageous for the subsequent selection of the cell of interest. After selectively growing the fusion cells, cells that produce an antibody to the compound of the present invention are selected. This selection is conducted by determining the presence or absence of the antibody of interest contained in the supernatant of the fusion cell culture by a method such as enzyme immunoassay or radioimmunoassay. The selected cells are subjected to, for example, limiting dilution method or soft agar culture method to obtain monoclones, thereby establishing a monoclonal-antibody-producing hybridoma cell line specific for 2-amino-3-[2-(α-mannopyranosyl)indole-3-yl]propionic acid.

The monoclonal antibody may be obtained by culturing an established cell line in a suitable medium and collecting the antibody from the culture. Alternatively, the cell line may be transplanted into the abdominal cavity of an animal and grown in ascites in order to collect the ascites and to recover the monoclonal antibody therefrom. The antibody in the culture or ascites may be, if necessary, purified prior to use. Purification may be conducted by various methods including salting-out fractionation using ammonium sulfate or the like, ion exchange chromatography, gel filtration column chromatography, affinity column chromatography using protein A or G, or affinity column chromatography using antigen-immobilized gel, the methods being used alone or in combination. The antibody can be produced in the above-described manners.

An example of the hybridoma that produces the monoclonal antibody of the invention is hybridoma KTM-250. This hybridoma has been deposited with the National Institute of Bioscience and Human-Technology, Agency of Industrial Science and Technology, MITI (Higashi 1-1-3, Tsukuba-shi, Ibaraki-ken, 305-0046, Japan) on Jul. 17, 1998 as FERM BP-6432. Hereinafter, the monoclonal antibody produced by hybridoma KTM-250 is simply referred to as KTM-250 antibody.

Hereinafter, a method for quantitating 2-amino-3-[2-(α-mannopyranosyl)indole-3-yl]propionic acid in a biological sample, for use in the test method according to the invention, will be described. The substance in the biological sample may be quantitated by high-performance liquid chromatography using the substance isolated/purified according to the method described above as a standard substance. The measurement instrument may be a general high-performance liquid chromatography instrument which may be equipped, for example, with a liquid transporting pump, a controller, a solvent mixer, a sample injector, a detector and a recorder. The liquid transporting system is desirebly a device that allows concentration-gradient elution. The column is a reverse-phase column or an ion-exchange column. Column filler is preferably porous silica, porous polymer or the like. The substituent of the filler is, for example, $C_{18}$ alkyl group, $C_8$ alkyl group, phenyl group, diphenyl group, cyanopropyl group, carboxymethyl group, sulfopropyl group, diethylaminoethyl group, or diethyl-(2-hydroxypropyl)aminomethyl group. The detection is conducted by a general detection such as fluorescent detection, absorbance detection, differential refraction detection or electrochemical detection.

If the collected biological sample is measured by high-performance liquid chromatography, the biological sample may directly be injected into the sample injector, or the biological sample may be subjected to pre-treatment. For example, the biological sample may be subjected to centrifugation and its supernatent may be used, or it may be used after filtration through a filter with a pore size of 10 μm or less, preferably 1 μm or less, more preferably 0.1 μm or less. A sample treated in a treatment column may also be used. The biological sample may be subjected to a general steps such as drying, redissolution, extraction, desalting and concentration.

Since the collected biological sample may be unstable, it is preferably added with a reducing agent such as vitamin C, or acid such as hydrochloric acid or perchloric acid.

A fluorescent substance such as N-methylserotonin may be added to the sample as the internal standard for the high-performance liquid chromatography. The solvent used in the high-performance liquid chromatography may be an organic solvent such as acetonitrile, an aqueous sovlent such as trifluoroacetic acid or heptafluorobutyric acid, or a buffer such as phosphate buffer, methane sulfonate buffer, formate buffer, acetate buffer or citrate buffer, which may be used alone or in combination.

Hereinafter, a quantitation method using the antibody will be described. The measurement employed in the present invention will be described.

2-Amino-3-[2-(α-mannopyranosyl)indole-3-yl] proiponate can immunologically be measured by using the antibody of the invention. Examples of the immunological measurement include, but are not limited to, various highsensitivity immunoassays such as radioimmunoassay using a radioisotope as a label, enzyme immunoassay using an enzyme, fluorescent immunoassay using a fluorescent substance, and luminescent immunoassay using a luminescent substance. Although most of known quantitations are applicable, competitive assays are most suitable. Competitive assays can be carried out in various manners. For example, a labeled antigen may compete with an antigen contained in the sample or with an antigen as a standard for binding to the antibody; an antigen from the sample or an antigen as a standard in the liquid phase may compete with an immobilized antigen for binding to the labeled antibody; or a labeled antigen may compete with an antigen in the sample or an antigen as a standard for binding to the immobilized antibody.

Hereinafter, a method for testing various biological functions will be described. Biological functions are determined from values obtained by quantitating 2-amino-3-[2-(α-mannopyrasyl)indole-3-yl]propionic acid levels in biological samples.

Examples of the biological sample include biological fluids such as blood, plasma, serum, urine, amniotic fluid, cerebrospinal fluid or cell extract, which are selected depending on purposes of the test.

The method of the present invention can be used for assaying an endogenous renal Glomerular filtration rate (hereinafter referred to as GFR).

GFR can be generally expressed as GFR=U×V/P (U=a level in urine; V=urine volume; P=a level in blood). Assay of GFR is performed by using as the indication a substance which can freely pass through the renal glomeruli without being degenerated (e.g., decomposed) in vivo and is neither excreted from the uriniferous tubule nor reabsorbed. Since the level of the substance in the glomerular filtrate is equal to that in blood (plasma), the amount of the substance which is excreted in urine during a certain period of time (1 minute) (U×V) is equal to that which is filtered through the glomeruli during the same period of time. Accordingly, this amount divided by the level in blood gives a glomerular filtration rate. Generally, test substances include endogenous substances such as creatinine and urea and exogenous substances such as inuline, sodium thiosulfate, and mannitol. Clearance values of these substances are used as GFRs. Since the urinary amount of a person is approximately proportionate to his/her body surface area, such GFR values may be corrected with the body surface area for clinical use. For calculation of urine volume, a value obtained by dividing the amount of a second complete micturition at a certain period of time (1 hour) after a first complete micturition by the time (i.e., 1 hour) (ml/minute) is used. For correction with the body surface area, a value obtained dividing an average body surface area of Japanese people (1.48 m² for adults) by the body surface area of a subject calculated from his/her height and weight may be used. For example, when creatinine is used, GFR is (65.0×1.44×1.48)/(0.9×1.40)=110 ml/min under the following conditions: urine volume, 1.44 ml/min; creatinine level in urine, 65.0 mg/dl; creatinine level in plasma, 0.9 mg/dl; and body surface area, 1.4 m².

If, among the substances above, an endogenous substance is produced in vivo at a certain level but exists in a certain level in blood (e.g., renal functions are in an abnormal state such that the endogenous substance cannot be filtered in the kidney), the endogenous substance accumulates in blood and thus its level increases in blood. Accordingly, the disorder of renal functions can be predicted by determining the level in blood and the amount in urine of the endogenous substance. Alternatively, if, regardless of normal renal functions, the level of an endogenous substance is increased in blood or urine, this abnormality may indicate any change in functions such as increased production and decreased metabolism of the substance. In this case, such indicators can be used for diagnosis of disorders. On the contrary, decreased levels of an endogenous substance in blood or urine indicate any change in functions such as decreased production and increased metabolism of the substance, thus such indicators can also be used for diagnostic of disorders. For these purposes, levels of an endogenous substance in blood and in urine (calculated from its level in urine and a urinary amount) may be determined alone or separately.

For testing renal functions, levels of such substances in, for example, serum are determined. Results of Example 3 below show that levels of the substance in sera from 99% of healthy persons (n=50) are within the range of 52–99 ng/ml while the levels in sera from 99% of patients (n=30) with renal dysfunction are within the range of 307–1403 ng/ml. Accordingly, for example, the level of the substance in serum of 100 ng/ml or more indicates a renal hypofunction.

For testing central nervous functions, the level of the substance in, for example, cerebrospinal fluid is determined. Results of Example 4 below show that levels of the substance in cerebrospinal fluids from 99% of healthy persons (n=22) are within the range of 72–188 ng/ml while the levels in cerebrospinal fluids from patients with spinocerebellar ataxia or metastatic brain tumor are 400 ng/ml or more. Accordingly, for example, the level of the substance in cerebrospinal fluid of 200 ng/ml or more indicates a central nervous hypofunction.

For test of pregnancy functions, the level of the substance in, for example, amniotic fluids is determined. Results of Example 5 below show that levels of the substance in amniotic fluids from 99% of healthy persons (n=21) are within the range of 113–593 ng/ml while the levels in amniotic fluids from 99% of pregnant patients with uremic syndrome (n=9) are in the range of 675–2147 ng/ml. Accordingly, for example the level of the substance in amniotic fluids of 600 ng/ml or more indicates pregnant hypofunction.

BEST MODES FOR CARRYING OUT THE INVENTION

Figure 1:
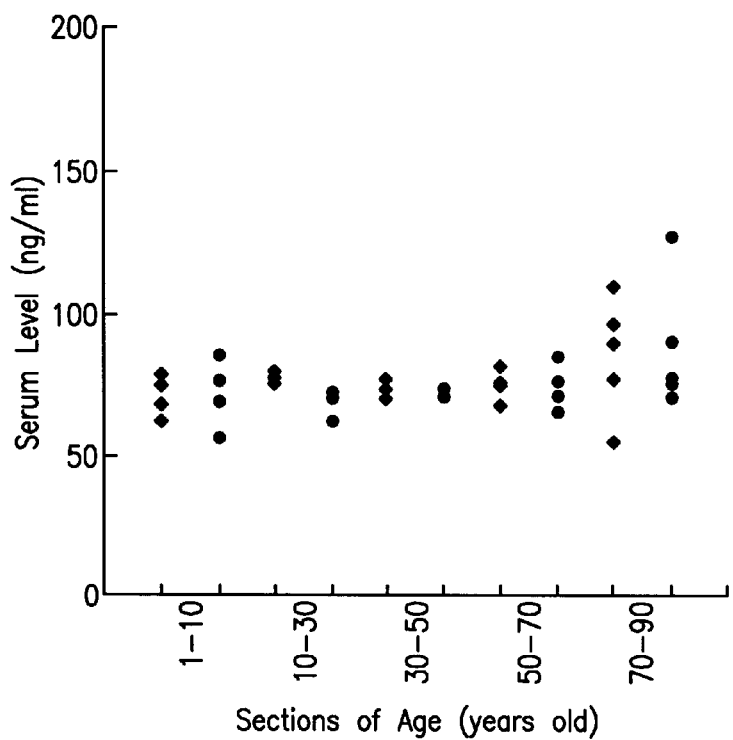
FIG. 1 shows a diagram illustrating the levels of 2-amino-3-[2-(α-mannopyranosyl)indole-3-yl]propionic acid in serum samples from healthy persons, showing differences between ages and between sexes of the subjects.

Hereinafter the present invention will be described by means of more particular Examples though the present invention should not be intended to be limited thereto.

EXAMPLE 1

Isolation and Purification of the Compound of the Present Invention

Isolation and purification of 2-amino-3-[2-(α-mannopyranosyl)indole-3-yl]propionic acid from healthy persons were performed as follows. First, 500 L of urine was concentrated to 10 L and filtered through a glass filter. The filtrate was mixed with 12 L of butanol/glacial acetic acid (5:1, v/v) solution. The butanol layer was separated, added with 2 kg of sodium tetraborate and left overnight. Then, the aqueous phase was collected, concentrated, and filtered through a glass filter. The filtrate was then applied to a Phenyl Sepharose-CL-4B column (4.2×50 cm) equilibrated with a solution of 5.0M ammonium chloride in water for elution, and fractionated. Fractions containing the target product were concentrated and filtrated on a glass filter. Next, the concentrated filtrate was applied to a Sephadex G-25 super fine column (4.2 cm×120 cm, Pharmacia) equilibrated with distilled water for elution, and then fractionated. Fractions containing the target product with conductivity of 5 mmho or less were collected, while those with conductivity of 5 mmho or more were concentrated again and fractionated with the Sephadex G-25 super fine column to give fractions containing the target product with conductivity of 5 mmho or less. The target fractions were concentrated, and applied to a cation exchange resin CM-Sepharose Past Flow column (4.2×50 cm, Pharmacia) equilibrated with distilled water for elution. Fractions containing the target product were collected, concentrated, and applied to an anion exchange resin DEAE-Sephacel column (4.2×50 cm, Pharmacia) equilibrated with distilled water for elution to collect fractions containing the target product which were then concentrated. The concentrate was subjected to HPLC (high performance liquid chromatography) [column: Radial-Pak C18 (8 mm×10 cm, Waters Corp.); development solvent: acetonitrile/water (1:9, v/v); flow rate: 1 ml/min] and the collection of fractions containing the target product was repeated. The collected product was purified again by collecting fractions containing the target product in the same manner as described above except that acetonitrile/water (1:45, v/v) was used as the development solvent in the above-described high performance liquid chromatography, and the collected fractions were concentrated to give 5 mg of the purified final product in a form of colorless syrup. The detection of the product obtained during the isolation and purification steps was performed by high performance liquid chromatography using the following conditions;

Column: Finepak SIL C18-T5 (4 mm×25 cm, JASCO Corporation)

Development solvent: Mixed solvent of acetonitrile and buffer (70 mM citric acid: 60 mM disodium phosphate=1:1, v/v, pH3.5) 0 min to 1.5 min; acetonitrile; buffer=96:4 (v/v) 1.5 min to 7.0 min; acetonitrile: buffer=92:8 (v/v) 7.0 min to 25.0 min; acetonitrile: buffer=88:12 (v/v)

Temperature: Room temperature

Flow rate: 1.5 ml/min

Detection: Fluorescence, excited at 302 nm, determined at 350 nm

Retention time: 6.8 min

EXAMPLE 2

Quantitation of the Compound of the Present Invention by High Performance Liquid Chromatography Standard solution of 2-amino-3-[2-(α-mannopyranosyl) indole-3-yl]propionic acid obtained in Example 1 above was prepared. Next, 350 μl of the standard solution was added to 500 μl of 0.1N hydrochloric acid containing 1% vitamin C, mixed with 50 μl of 40 μM N-methyl serotonin as an internal standard then 100 μl of 60% perchloric acid, and centrifuged at 3000 rpm at 4° C. The supernatant was filtered through a 0.22 μm filter to obtain a filtrate.

The filtrate was subjected to high performance liquid chromatography under the following conditions:

Column: Finepak SILC18-T5 (4 mm×25 cm, JASCO Corporation)

Development solvent: Mixed solvent of acetonitrile and buffer (70 mM citric acid: 60 mM disodium phosphate=1;1, v/v, pH3.5)
0–1.5 min: acetonitrile: buffer=96:4 (v/v)
1.5–7.0 min: acetonitrile: buffer=92:8 (v/v)
7.0–25.0 min: acetonitrile: buffer=88:12 (v/v)

Temperature: Room temperature

Flow rate: 1.5 ml/min

Detection: Fluorescence, excited at 302 nm, determined at 350 nm

The results showed a good linear relationship between the levels of 2-amino-3-[2-(α-mannopyranosyl)indole-3-yl] propionic acid in the samples and the fluorescence intensities, enabling the quantitation using the internal standard.

EXAMPLE 3

Quantitation of the Compound of the Present Invention in Patients with Renal Disease Sera from healthy persons and patients with renal disease were quantitated for the compound of the present invention. First, bloods were collected from the subjects and left to stand at room temperature for 30 minutes for coagulation. Next, the sera were collected by centrifugation at 3000 rpm for 10 minutes and stored at −80° C. until use. Sera from healthy persons (males and females, newborns to 90-year-old persons) were quantitated for the compound of the present invention in the same manner as that of Example 2 except that sera were used instead of the standard solution. The results are shown in FIG. 1 in which ◆ shows males and ● females, respectively. As shown in this figure, 76.3 ng/ml (SD 10.3) was obtained from males and 74.5 ng/ml (SD 12.6) from females. No difference was detected between ages or between sexes.

Figure 2:
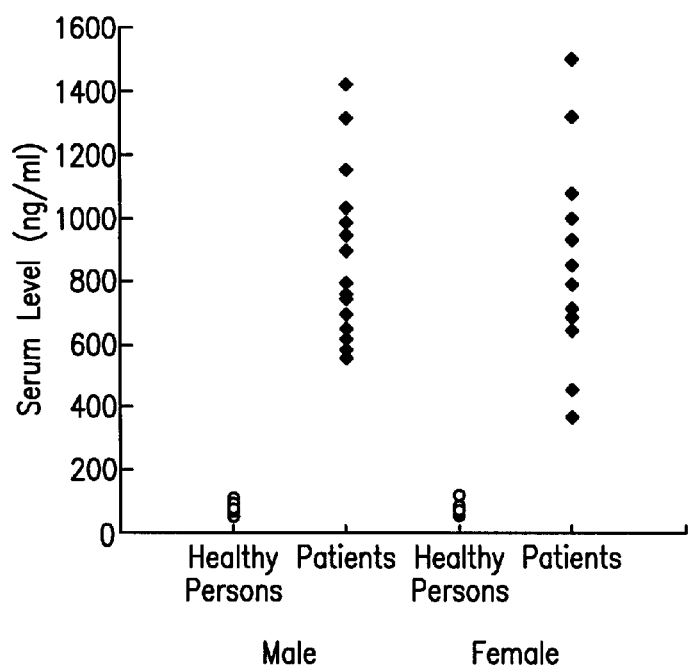
FIG. 2 shows a diagram illustrating the levels of 2-amino-3-[2-(α-mannopyranosyl)indole-3-yl]propionic acid in serum samples from healthy persons and patients with renal disease, showing differences between sexes.

Next, sera from patients with renal disease (17 males, average age of 53.9; 13 females, average age of 46.4) were quantitated for the compound of the present invention. The results are shown in FIG. 2 in which ○ shows the healthy persons and ◆ the patients with renal disease, respectively. As shown in this figure, the average value of 856 ng/ml (SD 247) was obtained for samples from male patients while 854 ng/ml (SD 305) for samples from female patients.

Since there is a significant difference between levels of the present compound in sera from healthy persons and patients with renal disease, renal functions can be evaluated based on the determined values of the compound of the present invention in the sera.

EXAMPLE 4

Figure 3:
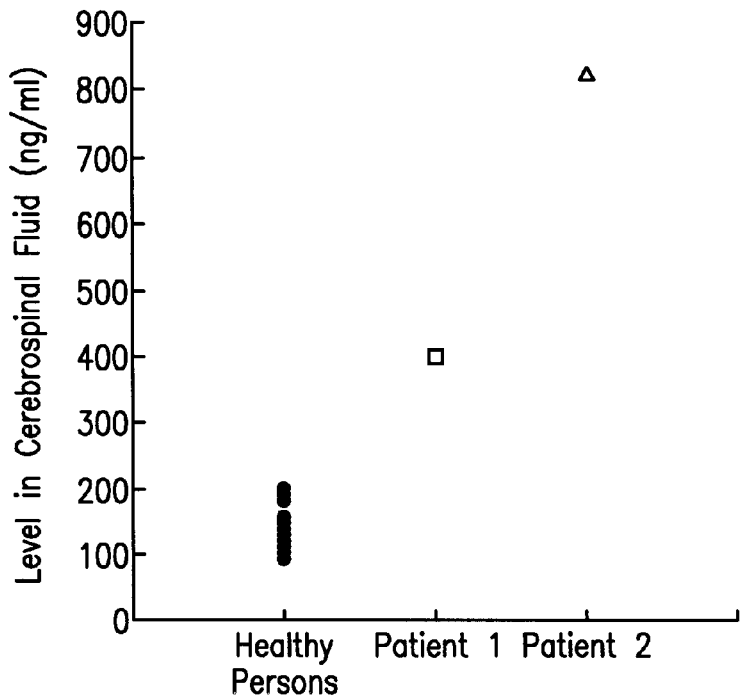
FIG. 3 shows a diagram illustrating the levels of 2-amino-3-[2-(α-mannopyranosyl)indole-3-yl]propionic acid in cerebrospinal fluid samples from healthy persons, a patient with spinocerebellar ataxia and a patient with metastatic brain tumor.

Quantitation of the Compound of the Present Invention in Patients with Central Nervous Disease Sera and cerebrospinal fluids from healthy persons and patients with central nervous disease were quantitated for the compound of the present invention. Both sera and cerebrospinal fluids were collected from 22 healthy persons, one patient with spinocerebellar ataxia and one patient with metastatic brain tumor, and quantitated for the compound of the present invention in the sera and the cerebrospinal fluids in the same manner as that of Example 2 except that sera or cerebrospinal fluids were used instead of the standard solution. The level the compound in the sera was determined to be 69.9 ng/ml (SD 13.8) which was not significantly different from the value determined in Example 3. The result of quantitation of the compound in cerebrospinal fluids is shown in FIG. 3 in which ●, □ and Δ show the healthy persons, the patient with spinocerebellar ataxia, and the patient with metastatic brain tumor, respectively. As shown in this figure, the level of the compound in cerebrospinal fluids from healthy persons was determined to be 130.4 ng/ml (SD 29.1). The level of the compound in cerebrospinal fluid from the patient with spinocerebellar ataxia was determined to be 399.4 ng/ml. The level of the compound in cerebrospinal fluid from the patient with metastatic brain tumor was determined to be 822.6 ng/ml.

Since there is a great difference between levels of the present compound in cerebrospinal fluids from a healthy person and a patient with central nervous disease, central nervous functions can be evaluated based on determined values of the compound of the present invention in cerebrospinal fluids.

EXAMPLE 5

Figure 4:
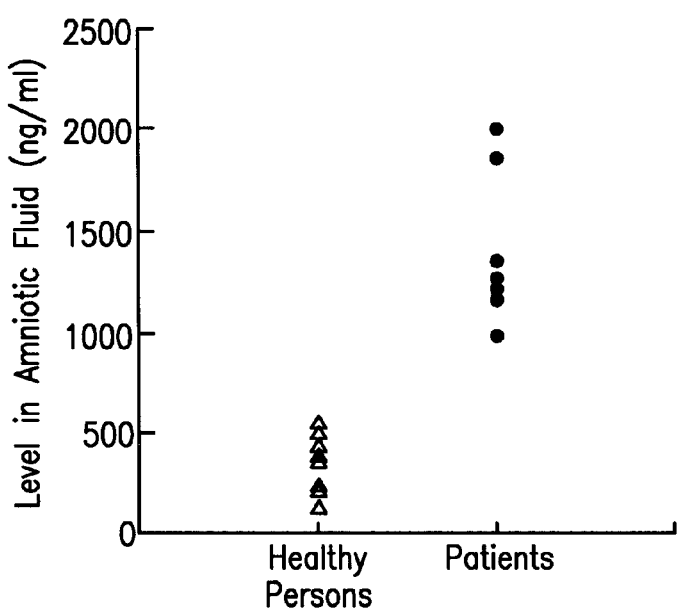
FIG. 4 shows a diagram illustrating the levels of 2-amino-3-[2-(α-mannopyranosyl)indole-3-yl]propionic acid in amniotic fluid samples from healthy pregnant persons and pregnant patients with uremic syndrome.

Quantitation of for the Compound of the Present Invention in Pregnant Patients with Uremic Syndrome Amniotic fluids from pregnant healthy persons and pregnant patients with uremic syndrome staying in hospital were quantitated for the compound of the present invention. Amniotic fluids were collected from 21 healthy persons (21–41 weeks old) and 9 pregnant patients with uremic syndrome (24–49 weeks old), and assayed for the compound of the present invention. The quantitation was performed in the same manner as that of Example 2 except that amniotic fluids were used instead of the standard solution. The results are shown in FIG. 4 in which Δ and ● show the healthy persons and the pregnant patients with uremic syndrome, respectively. As shown in this figure, 353.0 ng/ml (SD 120.1) was obtained for the healthy persons while 410.7 ng/ml (SD 367.9) for the pregnant patients with uremic syndrome.

Since there is a significant difference between the levels of the present compound in amniotic fluids from a healthy person and a pregnant patient with uremic syndrome, developmental functions of a fetus can be evaluated from determined values of the compound of the present invention in amniotic fluids.

EXAMPLE 6

Preparation of Monoclonal Antibody
a) Preparation of Antigen for Immunization

An equal amount of compounds (XIII-1) and (XIII-2) synthesized in Example 10 were mixed together to give 2-amino-3-[2-(α-mannopyranosyl)indole-3-yl]propionic acid (the mixture of 2R and 2S thereof hereinafter simply referred to as 2-amino-3-[2-(α-D-mannopyranosyl)indole-3-yl]propionic acid). Then, 0.5 mg of the 2-amino-3-[2-(α-D-mannopyranosyl)indole-3-yl]propionic acid was dissolved in 50 μl of methanol and then mixed with 0.5 ml of aqueous solution of keyhole limpet hemocyanin (available from Calbiochem Co., hereinafter simply referred to as KLH). The mixture was adjusted to pH 7–8, then added with 20 mg of EDC (1-ethyl-3-(3-dimethylaminopropyl) carbodiimide, available from Pierce Chemical Company) and allowed to react for 6 hours at room temperature. After the reaction was completed, the reaction mixture was dialyzed against 10 mM phosphate buffer solution containing 140 mM of NaCl (pH7.4, hereinafter simply referred to as PBS) to give 2-amino-3-[2-(α-D-mannopyranosyl)indole-3-yl]propionic acid-KLH.

Similarly, 2-amino-3-[2-(α-D-mannopyranosyl)indole-3-yl]propionic acid-BSA was prepared in the same manner as described above except that bovine serum albumin (hereinafter referred to as BSA, available from Sigma Chemical Company) was used instead of KLH.
b) Preparation of Monoclonal Antibody Mixture consisting of equal amounts of Freund's complete adjuvant (ICN, available from Biochemical Corp.) and 2-amino-3-[2-(α-D-mannopyranosyl)indole-3-yl]propionic acid-KLH was intraperitoneally or subcutaneously (to the backs of mice) administered to Balb/c mice (6 weeks old, male: available from SLC Corp.) at 0.1 mg/mouse. Then, the mixture of Freund's incomplete adjuvant (ICN, available from Biochemical Corp.) and 2-amino-3-[2-(α-D-mannopyranosyl)indole-3-yl]propionic acid-KLH was subcutaneously administered to the backs of the mice at 0.1 mg/mouse every three weeks, twice in total. Three weeks later, a solution of 2-amino-3-[2-(α-mannopyranosyl)indole-3-yl]propionic acid-KLH in PBS was administered to their caudal veins at 0.1 mg/mouse and after three days, antibody-producing cells were obtained from their spleens.

The spleens were sterilely extracted from the immunized mice, loosen in serum-free RPMI-1640 medium (available from Nissui Pharmaceutical), passed through a 100-mesh screen to separate each cell, suspended in hypotonic solution to lyse erythrocytes, and washed (×3) in serum-free RPMI-1640 medium by centrifugation.

On the other hand, mouse myeloma cells P3U1 (available from Dainippon Pharmaceutical) were cultured in RPMI-1640 medium containing 10% fetal calf serum (hereinafter referred to as "FCS", available from GIBCO), then harvested at the logarithmic growth phase, and washed (×3) in RPMI-1640 medium without serum by centrifugation.

Mixture of the antibody-producing cells and mouse myeloma cells P3U1 (10:1) were centrifugated at 1,200 rpm for 5 minutes to remove the culture medium. The cell residue was slowly added with 1 ml of 50% polyethyleneglycol 1500 solution (Boehringer Mannheim Co.), then gradually with 50 ml of serum-free RPMI-1640 medium, and centrifuged at 1,200 rpm for 5 minutes to remove the medium. The resultant cells were suspended at $1 \times 10^6$ cells/ml in HAT medium ($1 \times 10^{-4}$M hypoxanthine, $4 \times 10^{-7}$ M aminopterin and $2 \times 10^{-5}$ M thymidine in 10%-FCS-containing RPMI-1640 medium) and dispensed into a 96-well microplate at 200 μl/well. Subsequently, those cells were continuously cultured at 37° C. in air containing 5% carbon dioxide in a $CO_2$ incubator. Observation after 10 days showed that colonies of hybridoma were formed in all of the wells.
c. Assay Selection of a well containing cells which produce the antibody of interest was performed as follows. First, 50 μl of 2-amino-3-[2-(α-D-mannopyranosyl)indole-3-yl]propionic acid-BSA conjugate solution [20 μg/ml 0.1 M carbonate buffer, pH9.5] was dispensed into a 96-well microtiterplate and left to stand at 4° C. overnight. After washing the plate three times with PBS, 250 μl of 1% BSA/PBS solution was dispensed into the wells which were then left to stand for 1 hour at room temperature. Subsequently, each well was washed three times with PBS to prepare a reaction plate. To the reaction plate was added 50 μl of culture supernatant 11-fold diluted with PBS containing 0.1% BSA and the dilution was left to stand for reaction at room temperature for 3 hours. After the reaction was completed, the plate was washed five times with PBS containing 0.05% Tween 20. Then, 50 μl of POD labeled-anti-mouse immunogloblins-rabbit IgG (DAKO) was added to the plate for reaction at room temperature for 1 hour. After the reaction, the plate was washed five times with PBS containing 0.05% Tween 20, 50 μl of 10-N-methylcarbamoyl-3,7-dimethylamino-10H-phenothiazine solution (available from Kyowa Medics Co., Ltd., hereinafter referred to as MCDP) was added to the plate for reaction at room temperature for 30 minutes. Finally, 50 μl of reaction stopper was added to the plate which was then determined for absorbance at 660 nm on microplate reader (Corona Electrics Co., Ltd.). Five of 276 wells were found to have high reactivity, showing absorbance of 1.0 or greater.

d. Cloning

Cloning was performed by limiting dilution analysis. High reactivity cells in the above-described wells were diluted in RPMI-1640 medium containing 10% FCS and thymocytes ($1 \times 10^7$ cells/ml) to the concentration of 0.5 cell/ml. The dilution was dispensed into each well of a 96-well microplate at 200 μl/well and cultured at 37° C. in a carbon dioxide incubator in air with 5% carbon dioxide After 10–14 days of incubation, all the wells were observed to select those in which one colony was formed. Then, culture supernatant of the selected wells was assayed as described in c) assay above for selection of wells containing cell lines which produce the antibody of interest. Additionally, the above procedure was repeated twice to establish monoclonal antibody-producing cell lines which stably produce the antibody of interest. As a result, a total of five cell lines were obtained. The antibodies in the culture supernatant which were produced by the obtained cell lines were determined for their immunoglobulin classes by using a monoclonal antibody typing kit (Zymed Laboratories Inc.). All of the cell lines were confirmed to produce IgG-type antibodies.

e. Purifying the Antibodies

Balb/c mice (8 weeks old or more, male) were intraperitoneally injected with pristane (2, 6, 10, 14-tetramethylpentadecane, available from Wako Pure Chemical Industries., Ltd.) at 0.5 ml/mouse and bred for 2 weeks. These mice were inoculated with either cell line at $1 \times 10^6$ cells/mouse. After 7–14 days when enough ascites was stocked in their peritonea, the ascites was collected from the peritonea with a 18G injector and centrifuged at 3,000 rpm for 10 minutes to collect supernatant. The supernatant was then diluted (3×) with a binding buffer (3M, NaCl, 1.5M glycine, pH8.9) and allowed to flow through a protein A column equilibrated with the binding buffer. After washing the column with PBS, antibodies were eluted with 50 mM glycine/HCl buffer (pH2.5). The eluted solution was immediately neutralized with 1M phosphate buffer (pH7.5). Collected antibody solution was sufficiently dialyzed against PBS to obtain purified monoclonal antibodies.

f. Confirming the Specificity

First, 50 μl of 2-amino-3-[2-(α-D-mannopyranosyl) indole-3-yl]propionic acid-BSA conjugate solution (20 μg/ml, 0.1M carbonate buffer, pH9.5) was dispensed into a 96-well microtiter plate (available from NUNC) and left to stand at 4° C. overnight. After washing the plate with PBS (×3), 250 μl of 1% BSA/PBS solution was dispensed into the plate and left to stand at room temperature for 1 hour. Then, the plate was washed with PBS (×3) to be used as a reaction plate. Next, 50 μl of 0.1M phosphate buffer (pH 7.4) containing varied concentrations of test sample/0.1% BSA was dispensed into the reaction plate into which 50 μl of the monoclonal antibody prepared in e. Purifying the antibodies above (0.1M phosphate buffer containing 110 ng/ml 0.1% BSA, pH7.4) was added while stirring. The mixture was allowed to react at room temperature for 3 hours. After the reaction was completed, the plate was washed with PBS containing 0.05% Tween 20 (5×), and then 50 μl of POD labeled-anti-mouse immunoglobulins-rabbit IgG (DAKO) was added to the plate for reaction at room temperature for 1 hour. After reaction, the plate was washed with PBS containing 0.05% Tween 20 (5×), added with 50 μl of MCDP/50 mM citrate buffer solution (pH5.0), and the mixture was allowed to react at room temperature for 30 minutes. Finally, 50 μl of reaction stopper (ethyldiethyldithiocarbamate) was added to the plate of which absorbance was then determined at 660 nm by a microplate reader. The result showed concentration-dependent decrease in the absorbance. On the other hand, when the absorbance was determined using L-tryptophan and DL-mannose as the test samples at concentrations not more than 100 μg/ml, no decrease was confirmed in the absorbance, showing that the present antibody does not react with those substances.

EXAMPLE 7

Assay Using the Antibody of the Present Invention

Figure 5:
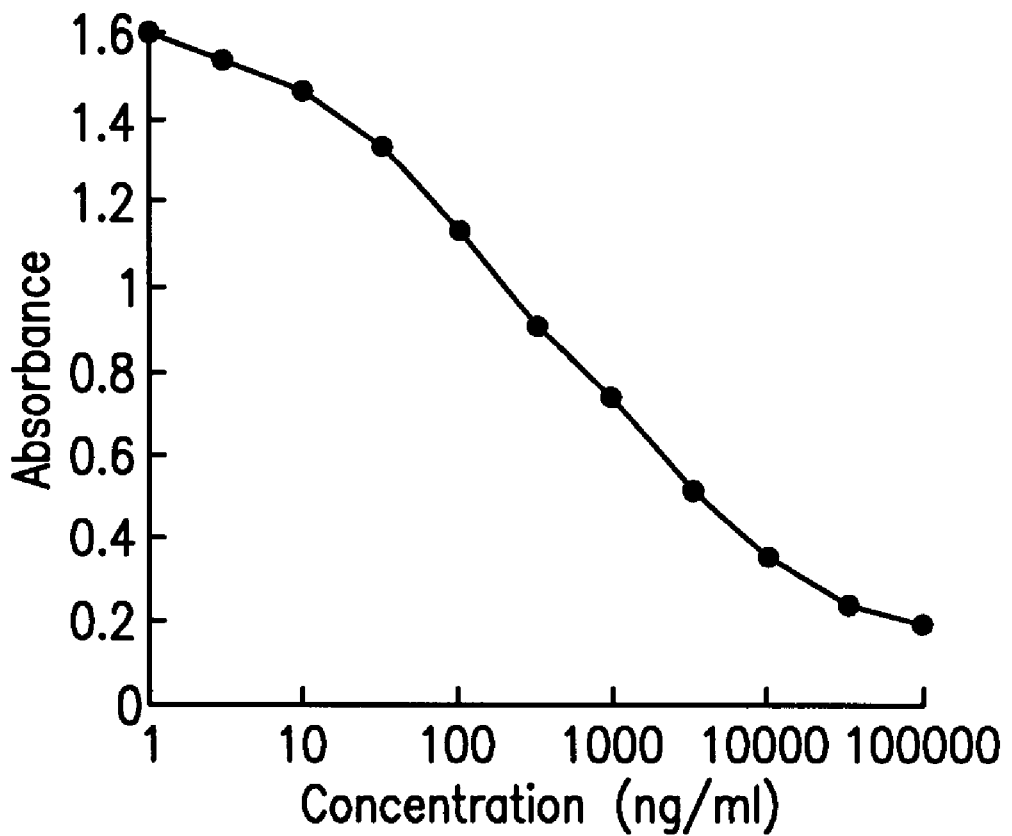
FIG. 5 shows a calibration curve obtained by determining the compound of the present invention using the antibody of the present invention.

Enzyme immunoassay was performed using the antibody prepared in Example 6. First, 50 μl of 2-amino-3-[2-(α-D-mannopyranosyl)indole-3-yl]propionic acid-BSA conjugate solution (20 μg/ml 0.1M carbonate buffer, pH9.5) was dispensed into a 96-well microtiter plate (NUNC. Corp.) and left to stand at 4° C. overnight. After washing the plate three times with PBS, 250 μl of 1% BSA/PBS solution was dispensed into the plate and left to stand at room temperature for 1 hour. Then, the plate was washed three times with PBS to be used as a reaction plate. Next, 50 μl of a test sample diluted with 0.1M phosphate buffer (pH 7.4) supplemented with varied concentrations of 2-amino-3-[2-(α-D-mannopyranosyl)indole-3-yl]propionic acid/0.1%BSA or 0.1M phosphate buffer supplemented with 0.1% BSA (pH7.4) was dispensed into the reaction plate into which 50 μl of the monoclonal antibody prepared in Example 6 (10 ng/ml, 0.1M phosphate buffer solution supplemented with 0.1% BSA, pH7.4) was added while stirring. The mixture was allowed to react at room temperature for 3 hours. Then, after the reaction was completed, the plate was washed five times with PBS containing 0.05% Tween 20, and then 50 μl of POD labeled-anti-mouse immunoglobulins-rabbit IgG (DAKO) was added to the plate for reaction at room temperature for 1 hour. After the reaction, the plate was washed five times with PBS containing 0.05% Tween 20, added with 50 μl of MCDP/50 mM citrate buffer solution (pH5.0), and the mixture was allowed to react at room temperature for 30 minutes. Finally, 50 μl of a reaction stopper (ethyl diethyldithiocarbamate) was added to the plate, and absorbance was then determined at 660 nm by a microplate reader. The calibration curve is shown in FIG. 5 in which the concentration of 2-amino-3-[2-(α-D-mannopyranosyl)indole-3-yl]propionic acid was indicated as a concentration of single compound.

EXAMPLE 8

GFR Assay

Eighteen patients with non-renal disease were assayed for the levels of 2-amino-3-[2-(α-mannopyranosyl)indole-3-yl]

propionic acid in their urine and sera as described in Example 7. Urine samples stored for 24 hours were used. Volumes of those samples were determined and then partially stored at −80° C. until assay. Upon use, the frozen urine samples were thawed at 37° C. and kept warm. Subsequently, after sufficient stirring and mixing, the samples were centrifuged at 3000 rpm for 10 minutes to remove impurities. The resultant supernatants were used as samples. Serum samples were collected from the patients' blood, left to stand at room temperature for 30 minutes for coagulation, and centrifuged to collect sera which were stored at −80° C. until use.

As a comparative example, creatinine levels in the same samples were assayed. The assay was performed on HITACHI Type 7070 biochemical autoanalyzer (Hitachi Koki Co., Ltd.) using a creatinine assay kit for an enzymatic assay (Determiner Cr633, Kyowa Medex Co., Ltd.) according to the manufacture's specification. The clearance was calculated as follows:

Clearance View=(level in urine×urine volume)/(24×60×serum level)

EXAMPLE 9

Assay of Excreted Amount in Urine

Healthy persons (male and female, from newborn to 90 year-old) were assayed for levels of 2-amino-3-[2-(α-mannopyranosyl)indole-3-yl]propionic acid in their urine as described in Example 7, to evaluate the usefulness of the method of the present invention for measurement of renal functions. Urine samples stored for 24 hours were pooled, their volumes were determined, and then partially stored at −80° C. until use. Upon use, the frozen urine samples were thawed and kept warm at 37° C. Subsequently, after sufficient stirring and mixing, the samples were centrifuged at 3000 rpm for 10 minutes to remove impurities. The resultant supernatants were used as samples. As a comparative example, creatinine levels in the same test samples were assayed. The assay was performed on HITACHI Type 7070 biochemical autoanalyzer (Hitachi Koki Co., Ltd.) using

TABLE 1

| subject | creatinine in serum mg/dl | the present compound in serum nmol/ml | creatinine in urine mg/dl | the present compound in urine nmol/ml | urine amount ml | clearance (ml/min) creatine | clearance (ml/min) the present compound |
|---|---|---|---|---|---|---|---|
| 1 | 0.71 | 0.213 | 69.9 | 12.989 | 1541 | 105.4 | 65.3 |
| 2 | 0.84 | 0.226 | 183.1 | 33.653 | 700 | 106.0 | 72.3 |
| 3 | 0.40 | 0.159 | 39.0 | 7.573 | 1600 | 108.3 | 52.8 |
| 4 | 0.61 | 0.240 | 50.1 | 11.677 | 1900 | 108.4 | 64.2 |
| 5 | 0.80 | 0.240 | 48.9 | 7.195 | 2600 | 110.4 | 54.2 |
| 6 | 0.50 | 0.193 | 21.2 | 4.242 | 3800 | 111.9 | 58.1 |
| 7 | 0.40 | 0.166 | 51.9 | 14.862 | 1300 | 117.1 | 80.8 |
| 8 | 0.70 | 0.280 | 30.5 | 19.188 | 1350 | 40.8 | 64.3 |
| 9 | 0.80 | 0.200 | 70.2 | 7.595 | 2010 | 122.5 | 53.0 |
| 10 | 0.56 | 0.319 | 32.0 | 10.649 | 3113 | 123.5 | 72.3 |
| 11 | 0.70 | 0.279 | 74.1 | 14.349 | 1700 | 125.0 | 60.7 |
| 12 | 0.72 | 0.279 | 48.2 | 13.645 | 2700 | 125.5 | 91.7 |
| 13 | 0.70 | 0.319 | 138.8 | 27.103 | 950 | 130.8 | 56.1 |
| 14 | 0.63 | 0.319 | 46.5 | 16.348 | 2500 | 128.1 | 89.1 |
| 15 | 0.70 | 0.193 | 100.2 | 12.726 | 1350 | 134.2 | 61.9 |
| 16 | 0.64 | 0.186 | 63.5 | 11.931 | 2000 | 137.8 | 89.2 |
| 17 | 0.40 | 0.193 | 142.0 | 26.935 | 800 | 197.2 | 77.6 |
| 18 | 0.80 | 0.309 | 88.0 | 15.040 | 2000 | 152.8 | 67.7 |
| Average | 0.65 | 0.24 | 72.12 | 14.87 | 1884.11 | 121.43 | 68.40 |

As shown in Table 1, the present compound showed, similar to the conventional creatine clearance, a limited range of clearance values.

creatinine assay kit for an enzymatic assay (Determiner Cr633, Kyowa Medex Co., Ltd.) according to the manufacture's specification. The results are shown in Table 2 below.

TABLE 2

| | the present compound (μg/day) | | | | creatinine (mg/day) | | | |
|---|---|---|---|---|---|---|---|---|
| age | male | | female | | male | | female | |
| (each = 5) | average | SD | average | SD | average | SD | average | SD |
| 0–10 | 4095 | 1876 | 4111 | 848 | 387 | 190 | 245 | 82 |
| 10–30 | 4581 | 2054 | 4520 | 1344 | 1066 | 318 | 609 | 212 |
| 30–50 | 4498 | 1673 | 4824 | 1590 | 1219 | 430 | 742 | 212 |
| 50–70 | 4647 | 1717 | 4412 | 1495 | 893 | 310 | 684 | 213 |
| 70–90 | 4622 | 1786 | 4666 | 1525 | 599 | 215 | 515 | 166 |
| 0–90 | 4488 | 1838 | 4507 | 1408 | 833 | 430 | 559 | 254 |

SD: standard deviation

As shown in Table 2 above, it was found that male persons showed higher creatinine values and that elder subjects showed higher creatinine levels although the level decreased from a time point of a certain senior age. The change in the creatinine level seems to be proportional to the change in the mass of muscle. On the other hand, the average excretion amount of the present compound per day is 4.5 mg/day This level had no significant difference between male and female nor among different ages. Accordingly, this level was proved to be a good indication.

EXAMPLE 10

Synthesizing 2-amino-3-[2-(α-D-mannopyranosyl) indole -3-yl]propionic Acid [Compound XIII]

Steps 1 and 2: Synthesis of 1-C-[1-(phenylsulfonyl) indole-2-yl]-2,3,4,6-tetra-O-benzyl-D-mannopyranose [Compound (IV) wherein $R^1$ to $R^4$ are benzyl and $R^5$ is phenylsulfonyl]

First, 6.93 g (26.93 mmol) of 1-(phenylsulfonyl)indole [compound (II) wherein X is hydrogen and $R^5$ is phenylsulfonyl] was dissolved in tetrahydrofuran (220 ml) and cooled to about −78° C. in dry ice-acetone. Subsequently, 1.5M lithium isopropylamide-cyclohexane solution (17 ml: 25.50 mmol) was added dropwise to the mixture and stirred for about 5 minutes to prepare lithium reagent [compound (III) wherein M is lithium and $R^5$ is phenylsulfonyl] according to the method described in *J. org. Chem.*, 47, 757 (1982). The lithium reagent [compound (III) wherein M is lithium and $R^5$ is phenylsulfonyl] was added with a solution of 2,3,4,6-tetra-O-benzyl-D-manno-δ-lactone [compound (I) wherein $R^1$ to $R^4$ are benzyl] 11.40 g (21.17 mmol) in toluene (220 ml) and stirred at −78° C. for 30 minutes. Then, an aqueous saturated solution of ammonium chloride was added to the mixture which was then extracted with diethylether. The ether solution was washed with saturated saline and dried on anhydrous sodium sulfate. After removal of the solvent by distallation, the residue was fractionated by column chromatography on silica gel [silica gel: Merck Kieselgel 60 (230–400 mesh ASTM); elution solvent: n-hexane and ethyl acetate (4:1)] to give 3.51 g (recovery 31%) of the starting material and 7.74 g (yield 46%) of 1-C-[1-(phenylsulfonyl)indole-2-yl]-2,3,4,6-tetra-O-benzyl-D-mannopyranose [compound (IV) wherein $R^1$ to $R^4$ are benzyl and $R^5$ is phenylsulfonyl].

$^1$H-NMR (270 MHz, CDCl$_3$) δ (ppm) (diastereomer mixture of approximately 1.4:1): 3.55–5.00 (15H, m), ca. 6.84–7.66 (27H, m), 7.80–7.87 and 8.12–8.18 (2H, m), 8.02 and 8.20 (1H, d each, J=8 Hz each).

FAB-MS: 817 [M−H+Na]$^+$, 778 [M−OH]$^-$.

Step 3: Synthesis of 1-C-[1-(phenylsulfonyl)indole-2-yl]-2, 3,4,6-tetra-O-benzyl-D-mannitol [Compound (V) Wherein $R^1$ to $R^4$ are Benzyl and $R^5$ Is Phenylsulfonyl]

First, 7.74 g (9.72 mmol) of 1-C-[1-(phenylsulfonyl) indole-2-yl]-2,3,4,6-tetra-O-benzyl-D-mannopyranose [compound (IV) wherein $R^1$ to $R^4$ are benzyl and $R^5$ is phenylsulfonyl] was dissolved in tetrahydrofuran (240 ml). Then, 1.11 g (29.25 mmol) of lithium aluminum hydride was added to the mixture and stirred at about 0° C. for about 30 minutes. After the reaction was completed, a saturated aqueous solution of Rochelle salt was added to the reaction mixture which was then subjected to extraction with diethylether. The ether solution was washed with saturated saline and then dried on anhydrous sodium sulfate. After removal of the solvent by distillation, the residue was fractionated by column chromatography on silica gel [silica gel: Merck Kieselgel 60 (230–400 mesh ASTM); elution solvent: n-hexane and ethyl acetate (5:2)] to give 5.85 g (yield 75%) of 1-C-[1-(phenylsulfonyl)indole-2-yl]-2,3,4,6-tetra-O-benzyl-D-mannitol [compound (V) wherein $R^1$ to $R^4$ are benzyl and $R^5$ is phenylsulfonyl].

$^1$H-NMR (270 MHz, CDCl$_3$) δ (ppm) (diastereomer mixture of about 1.4:1): (major isomer) 2.87 (1H, br s: OH), 3.63–3.89 (1H, m: OH), 3.71 (1H, dd, J=10, 6 Hz), 3.77 (1H, dd, J=10, 4 Hz), 3.84 (1H, d, J=11 Hz), 3.95 (1H, dd, J=7, 3.5 Hz), 4.14 (1H, dd, J=6.5, 3.5 Hz), 4.18 (1H, d, J=11 Hz), 4.18–4.31 (1H, m), 4.51 (1H, d, J=6.5 Hz), 4.56 (2H, s), 4.69 (1H, d, J=11.5 Hz), 4.79 (1H, d, J=11.5 Hz), 4.86 (1H, d, J=12 Hz), 4.90 (1H, d, J=12 Hz), 5.68 (1H, br s), 6.83 (1H, s), 6.87–6.95 (2H, m), 7.02–7.51 (24H, m), 7.51–7.60 (2H, m), 8.18 (1H, d, J=8 Hz). (minor isomer) 3.62 (1H, dd, J=10, 5 Hz), 3.68 (1H, dd, J=10, 3.5 Hz), 3.82 (1H, dd, J=8, 4 Hz), 3.93 (1H, dd, J=4, 4 Hz). 4.12 (1H, ddd, J=8, 5, 3.5 Hz), 4.43–4.57 (1H, m), 4.46 (2H, s), 4.48 (1H, d, J=12 Hz), 4.53 (2H, s), 4.54 (1H, d, J=12 Hz), 4.64 (1H, d, J=12 Hz), 4.69 (1H, d, J=12 Hz), 5.78 (1H, d, J=6 Hz), 6.62 (1H, s), 7.08–7.46 (26H, m), 7.66–7.75 (2H, m).

FAB-MS: 820 [M+Na]$^+$, 798 [M+Na]$^+$, 780 [M−OH]$^+$.

IR (KBr) cm$^{-1}$: 1497, 1452, 1369, 1207, 1174, 1151, 1090, 1070, 1065, 1028, 746, 737, 698, 685, 590, 573, 563.

Step 4: Synthesizing (1R)-1,5-anhydro-1-C-[1-(phenylsulfonyl)indole-2-yl]-2,3,4,6-tetra-O-benzyl-D-mannitol [Compound (VI) Wherein $R^1$ to $R^4$ Are Benzyl and $R^5$ Is Phenylsulfonyl]

First, 5.85 g (7.33 mmol) of 1-C-[1-(phenylsulfonyl) indole-2-yl]-2,3,4,6-tetra-O-benzyl-D-mannitol [compound (V) wherein $R^1$ to $R^4$ are benzyl and $R^5$ is phenylsulfonyl] was dissolved in toluene (500 ml). Then, 0.70 g (3.68 mmol) of paratoluene sulfate monohydrate was added to the mixture and stirred at about 100° C. for about 1 hour. After the reaction was terminated, a saturated solution of sodium hydrogen carbonate in water was added to the reaction mixture which was then subjected to extraction with diethylether. The ether solution was washed with saturated saline and dried on anhydrous sodium sulfate. After removal of the solvent by distillation, the residue was fractionated by column chromatography on silica gel [silica gel: Merck Kieselgel 60 (230–400 mesh ASTM); elution solvent: dichloromethane] to give 3.31 g (yield 58%) of (1R)-1,5-anhydro-1-C-[1-(phenylsulfonyl)indole-2-yl]-2,3,4,6-tetra-O-benzyl-D-mannitol [compound (VI) wherein $R^1$ to $R^4$ are benzyl and $R^5$ is phenylsulfonyl].

$^1$H-NMR (270 MHz, CDCl$_3$) δ(ppm) 3.54 (1H, dd, J=10, 4 Hz), 3.86 (1H, dd, J=10, 6 Hz), 3.88 (1H, dd, J=9, 3 Hz), 3.92–4.02 (2H, m), 4.27 (1H, dd, J=6, 3 Hz), 4.53 (2H, s), 4.56 (1H, d, J=11.5 Hz), 4.56–4.64 (2H, m), 4.58 (1H, d, J=12 Hz), 4.65 (1H, d, J=12 Hz), 4.66 (1H, d, J=11.5 Hz), 6.01 (1H, d, J=6 Hz), 6.46 (1H, s), 7.14–7.42 (26H$_1$, m), 7.78–7.85 (2H, m), 8.11 (1H, dd, J=8, 1 Hz).

FAB-MS: 780 [M+H]$^{31}$ .

IR (KBr) cm$^{-1}$: 1497, 1452, 1369, 1309, 1217, 1205, 1174, 1146, 1120, 1092, 1053, 1026, 748, 737, 698, 687, 586, 573, 561.

Step 6: Synthesizing (1R)-1,5-anhydro-1-C-(2-indolyl)-2,3, 4,6-tetra-O-benzyl-D-mannitol [Compound (VII) Wherein $R^1$ to $R^4$ are benzyl]

First, 3.31 g (4.25 mmol) of (1R)-1,5-anhydro-1-C-[1-(phenylsulfonyl)indole-2-yl]-2,3,4,6-tetra-O-benzyl-D-mannitol [compound (VI) wherein $R^1$ to $R^4$ are benzyl and $R^5$ is phenylsulfonyl] was dissolved in ethanol (100 ml). Then, 33 ml of 50% aqueous sodium hydrate solution was added to the mixture and stirred at about 100° C. for about 1 hour. After the reaction was terminated, a saturated solution of ammonium chloride in water was added to the reacted mixture which was then subjected to extraction with dichloromethane. The extracted solution was washed with water and then dried on anhydrous sodium sulfate. After removal of the solvent by distillation, the residue was fractionated by column chromatography on silica gel [silica gel: Merck Kieselgel 60 (230–400 mesh ASTM); elution solvent: 0.3% methanol-dichloromethane] to give 2.06 g (yield 76%) of (1R)-1,5-anhydro-1-C-(2-indolyl)-2,3,4,6-tetra-O-benzyl-D-mannitol [compound (VII) wherein $R^1$ to $R^4$ are benzyl].

$^1$H-NMR (270 MHz, CDCl$_3$) δ(ppm): 3.51–3.64 (1H, m), 3.74 (2H, d, J=4.5 Hz), 3.88 (1H, dd, J=8, 2.5 Hz), 3.93 (1H, dd, J=8, 8 Hz), 4.16 (1H, dd, J=2.5, 2.5 Hz), 4.50 (1H, d, J=11 Hz), 4.55 (1H, d, J=12 Hz), 4.60 (1H, d, J=12 Hz), 4.62 (1H, d, J=12 Hz), 4.71 (1H, d, J=12 Hz), 4.71 (1H, d, J=12 Hz), 4.77 (1H, d, J=12 Hz), 4.83 (1H, d, J=12 Hz), 5.20–5.28 (1H, m), 5.79 (1H, br s), 7.01–7.48 (24H, m), 8.48 (1H, br s).

FAB-MS: 640 [M+H]$^+$.

IR (KBr) cm$^{-1}$: 1497, 1454, 1363, 1338, 1294, 1207, 1157, 1095, 1038, 1026, 912, 835, 802, 787, 748, 698.

Step 7: Synthesizing 2-hydroxyimino-3-[2-(2,3,4,6-tetra-O-benzyl-α-D-mannopyranosyl)indole-3-yl]propionic Acid Ethyl Ester [Compound (IX) Wherein $R^1$ to $R^4$ Are Benzyl and $R^6$ Is Ethyl]

First, 2.08 g (3.24 mmol) of (1R)-1,5-anhydro-1-C-(2-indolyl)-2,3,4,6-tetra-O-benzyl-D-mannitol [compound (VII) wherein $R^1$ to $R^4$ are benzyl] was dissolved in dichloromethane (160 ml). Then, 1.36 g (6.49 mmol) of 3-bromo-2-hydroxyiminopropionic acid ethyl ester [compound (VIII) wherein $R^6$ is ethyl] and 1.03 g (9.74 mmol) of sodium carbonate powder were added to the mixture and stirred at room temperature for about 1.5 hours. Then, a saturated aqueous solution of sodium hydrogen carbonate was added to the reaction mixture which was then subjected to extraction with dichloromethane. The extracted solution was washed with water and then dried on anhydrous sodium sulfate. After removal of the solvent by distillation, the residue was fractionated by column chromatography on silica gel [silica gel: Merck Kieselgel 60 (230–400 mesh ASTM); elution solvent: n-hexane and ethyl acetate (3:1)] to give 1.04 g (recovery 50%) of the starting material and 0.93 g (yield 37%) of 2-hydroxyimino-3-[2-(2,3,4,6-tetra-O-benzyl-α-D-mannopyranosyl)indole-3-yl]propionic acid ethyl ester [compound (IX) wherein $R^1$ to $R^4$ are benzyl and $R^6$ is ethyl].

$^1$H-NMR (270 MHz, CD$_3$OD) δ(ppm): 1.04 (3H, t, J=7 Hz), 3.85 (1H, dd, J=4, 2 Hz), 3.88–4.19 (9H, m), 4.12 (1H, d, J=12 Hz), 4.18 (1H, d, J=14 Hz), 4.41 (1H, d, J=11.5 Hz), 4.47 (1H, d, J=11.5 Hz), 4.50 (1H, d, J=12 Hz), 4.57 (1H, d, J=12 Hz), 4.61 (1H, d, J=12 Hz), 4.73 (1H, d, J=12 Hz), 5.56 (1H, d, J=9 Hz), 6.86–6.94 (2H, m), 6.94–7.39 (21H, m), 7.70 (1H, d, J=8 Hz), 10.26 (1H, br s).

FAB-MS: 769 [M+H]$^+$.

IR (KBr) cm$^{-1}$: 1720, 1497, 1454, 1369, 1336, 1309, 1248, 1203, 1124, 1093, 1088, 1074, 1026, 743, 698.

Step 8: Synthesizing 2-amino-3-[2-(2,3,4,6-tetra-O-benzyl-α-D-mannopyranosyl)indole-3-yl]propionic Acid Ethyl Ester [Compound (X) Wherein $R^1$ to $R^4$ Are Benzyl and $R^6$ Is Ethyl]

First, 1.73 g (2.25 mmol) of 2-hydroxyimino-3-[2-(2,3,4,6-tetra-O-benzyl-α-D-mannopyranosyl)indole-3-yl] propionic acid ethyl ester [compound (IX) wherein $R^1$ to $R^4$ are benzyl and $R^6$ is ethyl] was dissolved in tetrahydrofuran (225 ml)-water (25 ml). Then, aluminum amalgam prepared from 8.50 g (0.32 mmol) of aluminum was added to the mixture and stirred at 55° C. for about 0.5 hour. Then, the reacted solution was filtrated on Celite which was then washed with 10% ethanol-dichloromethane. The filtrate was then concentrated and the residue was fractionated by column chromatography on silica gel [silica gel: Merck Kieselgel 60 (230–400 mesh ASTM); elution solvent: 3% methanol-dichloromethane] to give 1.54 g (yield 90%) of 2-amino-3-[2-(2,3,4,6-tetra-O-benzyl-α-D-mannopyranosyl)indole-3-yl]propionic acid ethyl ester [compound (x) wherein $R^1$ to $R^4$ are benzyl and $R^6$ is ethyl].

$^1$H-NMR (270 MHz, CD$_3$OD) (diastereomer mixture of about 1.6:1) δ(ppm): (major isomer) 1.09 (3H, t, J=7 Hz), 3.10 (1H, dd, J=14.5, 8 Hz), 3.20 (1H, dd, J=14.5, 5 Hz), 3.64–3.86 (3H, m), 3.90–4.25 (8H, m), 4.37–4.72 (6H, m), 5.18 (1H, d, J=9 Hz), 6.81–6.94 (2H, m), 6.99–7.40 (21H, m), 7.53 (1H, d, J=8 Hz). (minor isomer) 1.06 (3H, t, J=7 Hz), 2.91 (1H, dd, J=14, 8 Hz), 3.29 (1H, dd, J=14, 6 Hz), 3.64–3.86 (3H, m), 3.90–4.25 (8H, m). 4.37–4.72 (6H, m), 5.15 (1H, d, J=g Hz), 6.81–6.94 (2H, m), 6.99–7.40 (21H, m), 7.53 (1H, d, J=8 Hz).

FAB-MS: 755 [M+H]$^+$.

IR (KBr) cm$^{-1}$: 1734, 1497, 1454, 1365, 1336, 1308, 1205, 1093, 1072, 1028, 743, 698.

Step 9: Synthesizing 2-[N-(carbobenzyloxy)amino]-3-[2-(2,3,4,6-tetra-O-benzyl-α-D-mannopyranosyl)indole-3-yl]propionic Acid Ethyl Ester [Compound (XI) Wherein $R^1$ to $R^4$ Are Benzyl, $R^6$ is ethyl and Ar Is Phenyl]

First, 1.54 g (2.04 mmol) of 2-amino-3-[2-(2,3,4,6-tetra-O-benzyl-α-D-mannopyranosyl)indole-3-yl]propionic acid ethyl ester [compound (X) wherein $R^1$ to $R^4$ are benzyl and $R^6$ is ethyl] was dissolved in chloroform (100 ml). Then, triethylamine (0.86 ml) was added to the mixture which was cooled to about −20° C. Subsequently, 50%V/V benzyl chloroformate-toluene solution (1.50 ml) was added to the mixture and stirred for about 15 minutes. After the reaction was terminated, a saturated aqueous solution of sodium hydrogencarbonate was added to the reaction mixture which was then subjected to extraction with dichloromethane. The extracted solution was washed with water and then dried on anhydrous sodium sulfate. After removal of solvent by distillation, the residue was fractionated by column chromatography on silica gel [silica gel: Merck Kieselgel 60 (230–400 mesh ASTM); elution solvent: n-hexane and ethyl acetate (3:1)] to give 1.72 g (yield 95%) of 2-[N-(carbobenzyloxy)amino]-3-[2-(2,3,4,6-tetra-O-benzyl-α-D-mannopyranosyl)indole-3-yl]propionic acid ethyl ester [compound (XI) wherein $R^1$ to $R^4$ are benzyl, $R^6$ is ethyl and Ar is phenyl].

$^1$H-NMR (270 MHz, CDCl$_3$) (diastereomer mixture of about 1.6:1) δ(ppm): (major isomer) 1.07 (3H, t, J=7 Hz), 3.15 (1H, dd, J=15, 4.5 Hz), 3.51 (1H, dd, J=15, 6.5 Hz), 3.67–5.21 (21H, m), 6.67–7.43 (28H, m), 7.53 (1H, d, J=8 Hz), 8.15 (1H, br s). (minor isomer) 1.23 (1H, t, J=7 Hz), 3.08 (1H, dd, J=14.5, 10.5 Hz), 3.35 (1H dd, J=14.5, 4.5 Hz), 3.67–5.21 (20H, m), 6.39 (1H, br d, J=5 Hz), 6.67–7.43 (28H, m), 7.65 (1H, d, J=8 Hz), 8.19 (1H, br s)

FAB-MS: 889 [M+H]$^+$.

IR (KBr) cm$^-$: 1722, 1716, 1524, 1520, 1516, 1497, 1454, 1367, 1336, 1303, 1250, 1207, 1086, 1072, 1028, 743, 698.

Step 10: Synthesizing (2R*)-2-[N-(carbobenzyloxy)amino]-3-[2-(2,3,4,6-tetra-O-benzyl-α-D-mannopyranosyl)indole-3-yl]propionic Acid [Compound (XII-1) Wherein $R^1$ to $R^4$ Are Benzyl and Ar Is Phenyl] and (2S*)-2 [N-(carbobenzyloxy)amino]-3-[2-(2,3,4,6-tetra-O-benzyl-α-D-mannopyranosyl)indole-3-yl]propionic Acid [Compound (XII-2) Wherein $R^1$ to $R^4$ Are Benzyl and Ar Is Phenyl]

First, 1.72 g (1.94 mmol) of 2-[N-(carbobenzyloxy)amino]-3-[2-(2,3,4,6-tetra-O-benzyl-α-D-mannopyranosyl)

indole-3-yl]propionic acid ethyl ester [compound (XI) wherein $R^1$ to $R^4$ are benzyl, $R^6$ is ethyl and Ar is phenyl] was dissolved in 1,2-dimethoxyethane (60 ml)-water (30 ml). Then, 0.24 g (5.82 mmol) of lithium hydroxide monohydrate was added to the mixture and stirred at room temperature for about 16 hours. After the reaction was terminated, 0.5N citric acid (30 ml) was added to the reacted mixture which was then subjected to extraction with dichloromethane. The extracted solution was washed with water and then dried on anhydrous sodium sulfate. After removal of solvent, the residue was fractionated by columun chromatography on silica gel [silica gel: Merck Rieselgel 60 (230–400 mesh ASTM); elution solvent: n-hexane, ethyl acetate and methanol (3:6:0.6)] to elute compound (XII-1) and then compound (XII-2) which were further purified by preparative thin layer chromatography [preparative thin layer plate: Merck Kieselgel 60 $F_{254}$ (1 mm thick); development solvent: n-hexane, ethyl acetate and methanol (3:6:0.5)] to give 0.66 g (yield 40%) of (2R*)-2-[N-(carbobenzyloxy)amino]-3-[2-(2,3,4,6-tetra-O-benzyl-α-D-mannopyranosyl)indole-3-yl]propionic acid [compound (XII-1) wherein $R^1$ to $R^4$ are benzyl and Ar is phenyl] and 0.29 g (yield 17%) of (2S*)-2-[N-(carbobenzyloxy) amino]-3-(2-(2,3,4,6-tetra-O-benzyl-α-D-mannopyranosyl)indole-3-yl]propionic acid [compound (XII-2) wherein $R^1$ to $R^4$ are benzyl and Ar is phenyl].

(2R*)-2-[N-(carbobenzyloxy)amino]-3-[2-(2,3,4,6-tetra-O-benzyl-α-D-mannopyranosyl)indole-3-yl]propionic acid [compound (XII-1) wherein $R^1$ to $R^4$ are benzyl and Ar is phenyl]

$^1$H-NMR (270 MHz, CD$_3$OD) δ(ppm): 3.17 (1H, dd, J=15, 4.5 Hz), 3.26 (1H, dd, J=15, 6 Hz), 3.62–3.76 (2H, m), 3.82–3.89 (1H, m), 3.90–4.22 (3H, m), 4.05 (1H, d, J=12 Hz), 4.22 (1H, d, J=12 Hz), 4.31 (1H, d, J=12 Hz), 4.39 (1H, d, J=12 Hz), 4.39 (2H, s), 4.41 (1H, d, J=12 Hz), 4.48–4.59 (1H, m), 4.64 (1H, d, J=12 Hz), 4.75 (1H, d, J=12 Hz), 4.92 (1H, d, J=12 Hz), 5.17 (1H, d, J=10 Hz), 6.79–6.88 (2H, m), 6.94–7.37 (26H, m), 7.66 (1H, d, J=8 Hz), 10.38 (1H, br s).

FAB-MS: 861 [M+H]$^+$.

IR (KBr) cm$^{-1}$: 1730, 1718, 1524, 1518, 1508, 1497, 1454, 1439, 1365, 1340, 1334, 1308, 1273, 1246, 1209, 1151, 1113, 1103, 1090, 1068, 1026, 744, 698.

(2S*)-2-[N-(carbobenzyloxy)amino]-3-[2-(2,3,4,6-tetra-O-benzyl-α-D-mannopyranosyl)indole-3-yl]propionic acid [compound (XII-2) wherein $R^1$ to $R^4$ are benzyl and Ar is phenyl]

$^1$H-NMR (270 MHz, CD$_3$OD) δ(ppm): 3.04 (1H, dd, J=14, 11 Hz), 3.23–3.29 (1H, m), 3.40 (1H, dd, J=14, 4 Hz), 3.66 (1H, dd, J=10, 6 Hz), 3.83–4.00 (3H, m), 4.04 (2H, s), 4.14–4.25 (2H, m), 4.32 (1H, d, J=12 Hz), 4.34 (1H, d, J=12 Hz), 4.38 (1H, d, J=12 Hz), 4.45 (1H, d, J=12 Hz), 4.48 (1H, d, J=12 Hz), 4.48–4.60 (1H, m), 4.60 (1H, d, J=12 Hz), 4.73 (1H, d, J=12 Hz), 4.89 (1H, d, J=12 Hz), 5.10 (1H, d, J=10 Hz), 6.57–6.69 (2H, m), 6.87–7.37 (26H, m), 7.66 (1H, d, J=8 Hz), 10.39 (1H, br

FAB-MS: 861 [M+H]$^+$.

IR (KBr) cm$^{-1}$: 1730, 1724, 1718, 1701, 1540, 1527, 1523, 1518, 1508, 1497, 1454, 1439, 1340, 1308, 1269, 1257, 1244, 1209, 1151, 1109, 1092, 1072, 1041, 1028, 743, 698.

Step 11(1): Synthesizing (2R*)-2-amino-3-[2-(α-D-mannopyranosyl)indole-3-yl]propionic Acid [Compound (XIII-1)]

To a solution of (2R*)-2-[N-(carbobenzyloxy)amino]-3-[2-(2,3,4,6-tetra-O-benzyl-α-D-mannopyranosyl)indole-3-yl]propionic acid [compound (XII-1) wherein $R^1$ to $R^4$ are benzyl and Ar is phenyl](181 mg (0.210 mmol)) in ethanol (45 ml) was added 20% palladium hydroxide-carbon catalyst (150 mg) and the mixture was stirred at about 60° C. for about 11 hours under atmospheric pressure in the presence of hydrogen. The reacted solution was filtrated on Celite and the filtrate was concentrated. The residue was fractionated by high performance liquid chromatography [column: YMC-Pack ODS-AM SH-365-10AM, 500×30 mm, S-10, 120 Å; temperature: room temperature; migrating layer: 5% acetonitrile-water; flow rate: 40 ml/min.; detection: 278 nm (UV)] and then freeze-dried to give 48 mg (yield 62%) of (2R*)-2-amino-3-[2-(α-mannopyranosyl)indole-3-yl] propionic acid [compound (XIII-1)].

$^1$H-NMR (500 MHz, D$_2$O) δ(ppm): 3.33 (1H, dd, J=15, 10 Hz), 3.58 (1H, dd, J=15, 5 Hz), 3.73 (1H, dd, J=13, 3 Hz), 3.91 (1H, ddd, J=9, 3, 3 Hz), 3.94 (1H, dd, J=5, 3 HZ), 4.06 (1H, dd, J=10, 5 Hz), 4.13 (1H, dd, J=5, 3 Hz), 4.32 (1H, dd, J=13, 9 Hz), 4.43 (1H, dd, J=8, 3 Hz), 5.19 (1H, d, J=8 Hz), 7.19–7.24, 7.29–7.34, 7.54 (1H, br d, J=8 Hz), 7.75 (1H, br d, J=8 Hz).

$^{13}$C-NMR (125 MHz, D$_2$O) δ(ppm): 28.1, 57.6, 61.4, 68.3, 69.9, 71.3, 72.9, 81.3, 110.6, 114.3, 121.1, 122.2, 125.3, 129.6, 135.8, 138.4, 176.9.

FAB-MS: 367 [M+H]$^+$.

IR (KBr) cm$^{-1}$: 1624, 1506, 1462, 1406, 1348, 1069, 1013, 748. $[α]_D^{26}$ +54.3° (c 0.64, H$_2$O)

Step 11 (2): Synthesizing (2S*)-2-amino-3-[2-(α-D-mannopyranosyl)indole-3-yl]propionic Acid [Compound (XIII-2)]

To a solution of (2S*)-2-[N-(carbobenzyloxy)amino]-3-[2-(2,3,4,6-tetra-O-benzyl-α-D-mannopyranosyl)indole-3-yl]propionic acid [compound (XII-2) wherein $R^1$ to $R^4$ are benzyl and Ar is phenyl](90.5 mg (0.11 mmol)) in ethanol (25 ml) was added 20% palladium hydroxide-carbon catalyst (75 mg) and the mixture was stirred at about 60° C. for about 11 hours under atmospheric pressure in the presence of hydrogen. The reacted solution was filtrated on Celite and the filtrate was concentrated. The residue was fractionated by high performance liquid chromatography [column: YMC-Pack ODS-AM SH-365–10AM, 500×30 mm, S-10, 120Å; temperature: room temperature; migrating layer: 5% acetonitrile-water; flow rate: 40 ml/min.; detection: 278 nm (UV)] and then freeze-dried to give 24 mg (yield 62%) of (2S*)-2-amino-3-[2-(α-D-mannopyranosyl)indole-3-yl] propionic acid [compound (XIII-2)].

$^1$H-NMR (500 MHz, D$_2$O) δ(ppm): 3.35 (1H, dd, J=15, 9 Hz), 3.55 (1H, dd, J=15, 5 Hz), 3.74 (1H, dd, J=12.5, 3 Hz), 3.90 (1H, ddd, J=9, 3, 3 Hz), 3.96 (1H, dd, J=5, 3 Hz), 4.01 (1H, dd, J=9, 5 Hz), 4.13 (1H, dd, J=S, 3 Hz), 4.25 (1H, dd, J=12.5, 9 Hz), 4.43 (1H, dd, J=8, 3 Hz), 5.18 (1H, d, J=8 Hz), 7.22 (1H, ddd, J=7, 7, 1 Hz), 7.32 (1H, ddd, J=7, 7, 1 Hz), 7.52–7.56, 7.73–7.77.

$^{13}$C-NMR (125 MHz, D$_2$O) δ(ppm): 28.4, 57.7, 61.5, 68.6, 70.1, 71.3, 72.9, 81.4, 110.8, 114.3, 121.1, 122.2, 125.3, 129.5, 135.8, 138.4, 177.1.

FAB-MS: 367 [M+H]$^+$.

IR (KBr) cm$^{-1}$: 1626, 1404, 1350, 1245, 1064, 913, 748. $[α]_D^{26}$ +39.5° (c 0.129, H$_2$O)

Reference Example 1

(Step 5) Synthesizing (1R)-1,5-anhydro-1-C-[1-(phenylsulfonyl)indole-2-yl]-2,3,4,6-tetra-O-benzyl-D-mannitol [Compound (VI) Wherein $R^1$ to $R^4$ Are Benzyl and $R^5$ is Phenylsulfonyl]

First, 131 mg (0.165mmol) of 1-C-[1-(phenylsulfonyl) indole-2-yl]-2,3,4,6-tetra-O-benzyl-D-mannopyranose [compound (IV) wherein $R^1$ to $R^4$ are benzyl and $R^5$ is phenyl sulfonyl]was dissolved in dichloromethane (8 ml) and cooled to −78° C. Then, 0.40 ml (2.48 mmol) of triethylsilane and 0.20 ml (1.63 mmol) BF$_3$-ether complex were added to the mixture and stirred while rising the temperature from −78° C. to room temperature over about 11 hours. Subsequently, a saturated aqueous solution of sodium hydrogencarbonate was added to the mixture which was then subjected to extraction with dichloromethane. The dichloromethane solution was washed with saturated saline and then dried on anhydrous sodium sulfate. After removal of the solvent by distillation, the residue was fractionated by column chromatography on silica gel [n-hexane and ethyl acetate (3:1)] to give a mixture of which 120 mg was further fractionated and purified by preparative thin layer chromatography [preparative thin layer plate: Merck Kieselgel 60 F$_{254}$ (1 mm thick); development solvent: 0.5% methanol-dichloromethane] to give 21 mg (yield 16%) of (1R)-1,5-anhydro-1-C-[1-(phenylsulfonyl)indole-2-yl]-2,3,4,6-tetra-O-benzyl-α-D-mannitol [compound (VI) wherein R$^1$ to R$^4$ are benzyl and R$^6$ is phenylsulfonyl].

Reference Example 2

(Step 6) Synthesizing (1R-1,5-anhydro-1-C-(2-indolyl)-2,3,4,6-tetra-O-benzyl-D-mannitol [Compound (VII) Wherein R$^1$ to R$^4$ Are Benzyl]

First, 49 mg (0.03 mmol) of (1R)-1,5-anhydro-1-C-[1-(phenylsulfonyl)indole-2-yl]-2,3,4,6-tetra-O-benzyl-D-mannitol [compound (VI) wherein R$^1$ to R$^4$ are benzyl and R$^5$ is phenylsulfonyl]was dissolved in methanol (6 ml). Then, 99 mg (4.07 mmol) of magnesium and 99 mg (1.85 mmol) of ammonium chloride were added to the mixture and stirred at room temperature for about 12 hours. After the reaction was terminated, a saturated solution of ammonium chloride in water was added to the reacted mixture which was then subjected to extraction with dichloromethane. The extracted solution was washed with water and then dried on anhydrous sodium sulfate. After removal of the solvent by distillation, the residue was separated and purified by preparative thin layer chromatography [preparative thin layer plate: Merck Kieselgel 60 F$_{254}$ (1 mm thick); development solvent: 1% methanol-dichloromethane] to give 19 mg (yield 46%) of (1R)-1,5-anhydro-1-C-(2-indolyl)-2,3,4,6-tetra-O-benzyl-D-mannitol [compound (VII) wherein R$^1$ to R$^4$ are benzyl].

INDUSTRIAL APPLICABILITY OF THE INVENTION

The present invention provides a method for evaluating biological functions such as renal function, central nervous function and developmental function of fetus by quantitating a level of the novel endogenous compound. The present invention also provides a method for immunologically quantitating the novel endogenous compound and provide an antibody used therefor. The present invention also provides a process for producing the antibody used in the method for immunologically quantitating the novel endogenous compound and provides the novel compound used therefor. Further, the present invention provides a hybridoma that produces an antibody to the novel endogenous compound. The present invention also provides a process for synthesizing the novel compound. Moreover, the present invention provides a novel intermediate for synthesis of the novel compound.

What is claimed is:

1. A method for testing a renal function, comprising the steps of:

(i) obtaining a serum sample from a mammal; and (ii) quantitating 2-amino-3-[2-(alpha-D-mannopyranosyl)indole-3-yl]propionic acid in the sample obtained in step (i), wherein a level of 100 ng/ml or more is indicative of a renal hypofunction related to glomerular filtration.

2. A method for testing a central nervous function, comprising the steps of:

(i) obtaining a cerebrospinal fluid sample from a mammal; and (ii) quantitating 2-amino-3-[2-(alpha-D-mannopyranosyl)indole-3-yl]propionic acid in the sample obtained in step (i), wherein a level of 200 ng/ml or more is indicative of a central nervous hypofunction related to spinocerebellar ataxia or metastatic brain tumor.

3. A method for testing a pregnancy function, comprising the steps of:

(i) obtaining an amniotic fluid sample from a mammal; and (ii) quantitating 2-amino-3-[2-(alpha-D-mannopyranosyl)indole-3-yl]propionic acid in the sample obtained in step (i), wherein a level of 600 ng/ml or more is indicative of uremic syndrome.

4. A method for measuring an endogenous renal glomerular filtration rate, comprising:

(i) obtaining urine and serum samples from a mammal;

(ii) quantitating 2-amino-3-[2-(alpha-D-mannopyranosyl)indole-3-yl]propionic acid in the samples obtained in step (i), and (iii) quantitating a urinary amount for a period of time from the mammal.

5. A method comprising the steps of:

(i) obtaining a biological sample from a mammal;

(ii) applying an antibody reactive with 2-amino-3-[2-(alpha-D-mannopyranosyl)indole-3-yl]propionic acid to the biological sample obtained in step (i); and (iii) immunologically quantitating 2-amino-3-[2-(alpha-D-mannopyranosyl)indole-3-yl]propionic acid in the sample after applying said antibody.

6. A method according to claim 5, wherein the antibody is a monoclonal antibody.

7. A method according to claim 5, wherein the antibody is produced by hybridoma KTM-250 (FERM BP-6432).

8. An antibody reactive with 2-amino-3-[2-(α-mannopyranosyl)indole-3-yl]propionic acid.

9. An antibody according to claim 8, wherein the antibody is a monoclonal antibody.

10. An antibody according to claim 8, wherein the antibody is a monoclonal antibody produced by hybridoma KTM-250 (FERM BP-6432).

11. A hybridoma which produces a monoclonal antibody reactive with 2-amino-3-[2-(α-mannopyranosyl)indole-3-yl]propionic acid.

12. A hybridoma according to claim 11, wherein the hybridoma is KTM250 (PERM BP-6432).

13. A method for producing an antibody reactive with 2-amino-3-[2-(α-mannopyranosyl)indole-3-yl]propionic acid comprising the steps of:

(i) immunizing a mammal with an immunogen comprising a compound represented by formulae (XV) or (XV'):

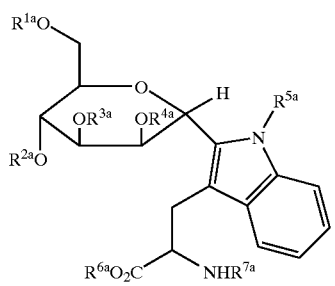

(XV)

or Formula (XV¹)

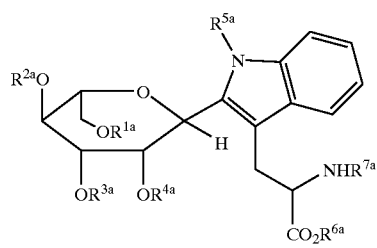

(XV')

(wherein $R^{1a}$ to $R^{4a}$ independently represent a hydrogen atom, a substituted or unsubstituted alkyl group, a substituted or unsubstituted alkenyl group, or a substituted or unsubstituted aryl group, $R^{5a}$ represents a hydrogen atom, a substituted or unsubstituted sulfamoyl group, a substituted or unsubstituted arylsulfonyl group, a substituted or unsubstituted alkoxycarbonyl group, or a substituted or unsubstituted alkoxymethyl group, $R^{6a}$ represents a hydrogen atom or a substituted or unsubstituted alkyl group; and $R^{7a}$ represents a hydrogen atom or a substituted or unsubstituted aralkyloxycarbonyl group) to produce an antibody reactive with 2-amino-3-[2-(α-mannopyranosyl)indole-3-yl]propionic acid; and thereafter (ii) isolating said antibody.

14. A process according to claim 13, wherein the immunogen comprises 2-amino-3-[2-(α-mannopyranosyl)indole-3-yl]propionic acid.

\* \* \* \* \*